(12) United States Patent
Keller et al.

(10) Patent No.: US 7,427,484 B2
(45) Date of Patent: Sep. 23, 2008

(54) GLOBAL REGULATOR OF SECONDARY METABOLITE BIOSYNTHESIS AND METHODS OF USE

(75) Inventors: Nancy P. Keller, Madison, WI (US); Jin Woo Bok, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 35 days.

(21) Appl. No.: 11/314,351

(22) Filed: Dec. 20, 2005

(65) Prior Publication Data

US 2007/0003999 A1    Jan. 4, 2007

Related U.S. Application Data

(62) Division of application No. 10/668,696, filed on Sep. 23, 2003, now Pat. No. 7,053,204.

(60) Provisional application No. 60/413,073, filed on Sep. 24, 2002.

(51) Int. Cl.
  *C12Q 1/68*  (2006.01)
  *C12N 1/14*  (2006.01)
  *C12N 1/15*  (2006.01)
  *C12N 15/80* (2006.01)
  *C12N 15/52* (2006.01)

(52) U.S. Cl. .................. 435/6; 435/254.1; 435/254.11; 435/254.3; 536/23.2

(58) Field of Classification Search .................. None
See application file for complete search history.

(56) References Cited

U.S. PATENT DOCUMENTS 5,171,686 A    12/1992    Cotty et al.
6,037,526 A    3/2000    Grimsley et al.
6,346,655 B1    2/2002    Hohn et al.
6,521,435 B1    2/2003    Okubara et al.
2002/0162136 A1    10/2002    Hohn et al.
2003/0022373 A1    1/2003    Jones et al.
2003/0131376 A1    7/2003    Okubara et al.
2004/0034884 A1    2/2004    Hohn et al.

OTHER PUBLICATIONS

Brown et al. (1996) Twenty-five co-regulated transcripts define a sterigmatocystin gene cluster in *Aspergillus nidulans*. Proc. Natl. Acad. Sci. USA, 93, 1418-1422.

Butchko et al. (1999) *Aspergillus nidulans* mutants defective in stc gene cluster regulation, Genetics, 153, 715-720.

(Continued)

*Primary Examiner*—Nashaat T. Nashed
*Assistant Examiner*—William W. Moore
(74) *Attorney, Agent, or Firm*—Quarles & Brady LLP

(57) ABSTRACT

The invention provides polypeptides and nucleic acids which identify and encode LaeA, a regulator of fungal secondary metabolite production which exhibits global control over secondary metabolite biosynthetic gene clusters. The invention further provides expression vectors, host cells, methods of increasing the production of secondary metabolites in an organism naturally producing a secondary metabolite or engineered to produce a secondary metabolite, and methods of identifying novel secondary metabolite biosynthesis gene clusters.

5 Claims, 5 Drawing Sheets

OTHER PUBLICATIONS

Frenandes et al., (1998) Sequence-specific binding by *Aspergillus nidulans* AflR, a C6 zinc cluster protein regulating mycotoxin biosynthesis. Mol. Microbiol. 28, 1355-1365.

Keller et al., (1997) Metabolic pathway Gene Clusters in Filamentous Fungi. fungal Genetics and Biology. 21, 17-29.

Kennedy et al., (1999) Modulation of polyketide synthase activity by accessory proteins during lovastatin biosynthesis. Science. 284, 1368-1372.

Lee et al. (2002) afsS is a traget of AfsR globally controls secondary metabolism in *Streptomyces coelicorlor* A3(2). Mol. Microbiol. 43, 1413-1430.

Pessi et al. (2001) Rsma Modulates Production of Virulence Determinants and N-Acylhomoserine Lactones in *Pseudomonas aeruginosa*. J. Bacteriol. 183, 6676-6683.

Skory et al. (1992) Isolation and characterization of a gene from *Aspergillus parasiticus* Appl. Environ. Microbiol. 58, 3527-3537.

Figure 1.

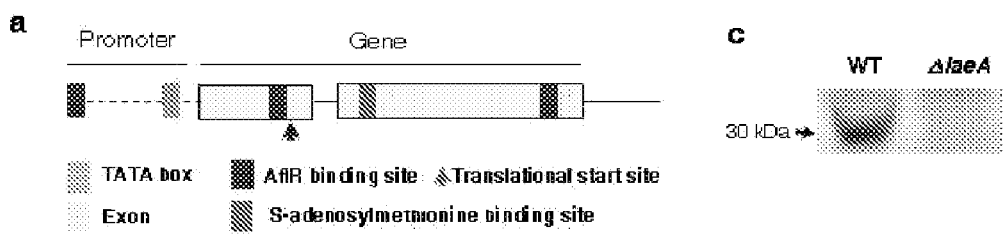

b

| | | |
|---|---|---|
| Aspergillus nidulans | DRLDIFHKLFTVARVSESLIYAPHP---TNGRFX.SLSCSTSIWAIEVANKYPDAF | 163 |
| Aspergillus fumigatus | DRLDIFHKLFTVARVSDGLIYAPHP---TNGRFX.SLSCSTSIWAIDVANKYPEAF | 147 |
| Neurospora crassa | ERLDDQYEIAKELMEGRNYFAPFSPKMSPRK-VX.SISCSTSTWAIDMGDEFPEAE | 117 |
| Magnaporthe grisea | NRIDLQHNLCMMTIGWKLYISPIDQRPVMR--VX.SISCSTSVWSMEA-DDHPEAH | 53 |
| Coccidioides immitis | DNLDLFHHVFNLTFGGRTFLAPIG--DNPQR-VX.SLSTSTSIWAMDFADEFPSAA | 92 |
| Fusarium sporotrichioides | ERLDLQHNLFLLTFDNKLGLAPPNLPDSKVKRVX.SLSTSTSIWAIDFGDDHSQTE | 81 |
| | :.:* :.: : . ,**:* *** *::: :...: | |
| Aspergillus nidulans | VAGVSLAPIQPPN--HPKNCEFYAPFSFEAPWAMGEDSWDLIHLQMGCGSVMGWP | 216 |
| Aspergillus fumigatus | VVGVSLAPIQPPN--HPRNCDFYAPFSFESLWALGEDSWDLIHMQMGSGSVASWP | 190 |
| Neurospora crassa | IIGTSLSPVQPDL--VPPNVRFFVE-SSSEEWIYAPNHFDYIHTRYTLGCWKDMK | 169 |
| Magnaporthe grisea | VIGISLSPIQPSLNSVPPNVSYYID-SVEAEWTYS-TPFDFIFTRMMLGCIRNWP | 105 |
| Coccidioides immitis | VIATSVSAIQPTL--VPXNLEFQID-SFCEPWTFRKESFDYIHARCIYGCSSDYP | 144 |
| Fusarium sporotrichioides | VIGVSLSPIQPNF--IPPNVRFLID-SIHEQWDFS-EPFDYIHSRMMNFIIPDWP | 132 |
| | : . *::..:** * * : * * :* *. : . | |

Figure 2.

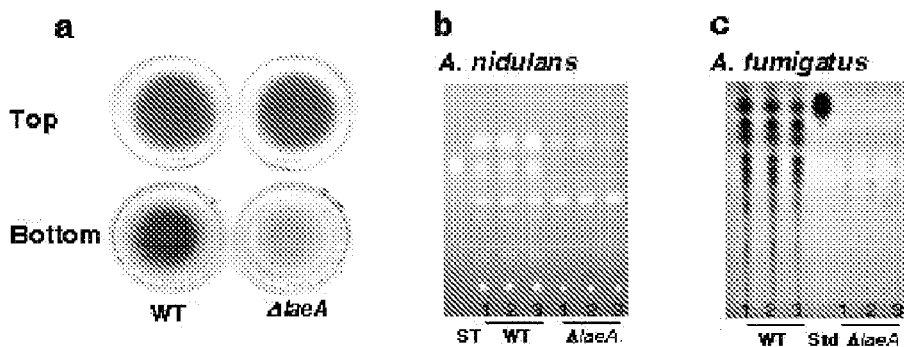

SEQUENCE LISTING

<160> NUMBER OF SEQ ID NOS: 21

<210> SEQ ID NO 1
<211> LENGTH: 3100
<212> TYPE: DNA
<213> ORGANISM: Aspergillus nidulans

<400> SEQUENCE: 1

| | | | | | |
|---|---|---|---|---|---|
| tttaaagcac | cgcagtagcg | caataccaag | cggaccgtcg | tcgagctgga | ctcgctcgac | 60 |
| tgccaggacg | cactcgagga | gggtcctgag | tgctgaatct | gatacaccac | ttgcagaggc | 120 |
| tagcagctga | cagcgccttc | gtcgtgcaga | gtagtctagt | agtctacagg | ggcccgatcc | 180 |
| tagtcatcct | agccatctta | gccatcctaa | ccttcctagc | cttcctagcc | atcctagtgc | 240 |
| ctccgccagg | cctttctcac | ccccgatctc | aaaaataata | ataataataa | aagaagtcga | 300 |
| cctcgtctgc | ttttgcaact | gcctcccgcc | ccgccccctt | cgcgcccgtg | ggcccaaccg | 360 |
| ggtcaagaga | gcggctgcga | caatcataaa | cttaaagaaa | agacggcgct | gcttgcttgc | 420 |
| ttgcctgctt | gcctgcttgc | ttgcttgtct | aaacgcccgt | cctgttgttg | tcccgcttcg | 480 |
| ctctctgttg | gtttatgggt | gtcagtccct | cgcgctcttc | cagcaccgtg | accgctactt | 540 |
| tttctcagcc | tgtcaatcgt | caatcttcaa | tttcccttgt | gggaggctct | gattcccgta | 600 |
| taattgaccc | ctcgccctcc | tgcatcaata | ttcggattcc | tgcttctatt | caacgggcag | 660 |
| aatttcttcc | agctcgtcca | cccctcactt | cgatgaacct | ctccttttc | ttttcaatcg | 720 |
| gctgtttaca | ttgtgttttc | tgggatctct | ggacgagtca | actagatctt | cagcttctgg | 780 |
| attgatctaa | cgaacattct | ttcggcttct | ggccccccgc | gctgctctgc | ctacccgccg | 840 |
| cccagcgcac | cccacggctt | tggtgacgat | ttgtatagtc | cactgttata | gtccactgaa | 900 |
| aacagttcct | tccactgttc | cactcggctg | tcgatctttg | taccctgttt | cgccgctgat | 960 |
| gtttgagatg | ggcccggtgg | gaactcgtct | ccccgccatg | acctctccag | cgcacaacca | 1020 |
| ctacagctac | cactctccca | cctccagcga | cagaggccgg | tcaaggcaga | actcggatgc | 1080 |
| catggacatc | cagtccatca | ctgaacgaga | gccggcgacc | agatacgcgg | ttgcgggcgg | 1140 |
| ccctgcgccc | tggaatcgca | acgggtctcc | gagcatgagc | cctatgtata | gcaagtacat | 1200 |
| ctctcttacc | cctccgtttc | tttctgcttt | tctaccaccc | catccctctt | tccagtctga | 1260 |
| gtccaggctt | gttccgcttg | aagtggctaa | tgtgatcctc | gtcttctctc | tttctgtgtt | 1320 |
| ttagcaattc | cgagcgaaac | cagtttcatg | aagagaacgg | acgcacctac | catggctttc | 1380 |
| gcagggaat | gtattttctt | ccgtgcgatg | agcaagaaca | ggatcgcctc | gacatcttcc | 1440 |
| ataagctatt | cacggtagcg | cgggtatcgg | agagtctgat | ctacgcgccc | catccaacca | 1500 |
| acggccggtt | tctggaccta | ggatgtggaa | ctggtatctg | ggcgatcgag | gtagcgaaca | 1560 |
| agtaccctga | tgcgtttgtc | gctggtgtgg | atttggctcc | tattcagcct | ccgaaccacc | 1620 |
| cgaagaactg | cgagttctac | gcgcccttcg | acttcgaagc | gccatgggcc | atggggagg | 1680 |

```
attcctggga tctaatccat ctgcagatgg gttgcggtag tgtcatgggc tggccaaact    1740
tgtatcgaag atattcgca catctccgtc ccggtgcctg gtttgagcag gttgagatcg    1800
atttcgagcc tcgatgtgat gatcggtcac tagatggaac ggcattgcgg cattggtacg    1860
attgtcttaa acaggcgaca gcagagacca tgcggccaat cgcccatagc tcccgcgata    1920
caataaaaga cctgcaggac gctgggttca cggagatcga ccatcaaata gtgggactcc    1980
cgctcaaccc gtggcatcag gacgaacacg agcggaaggt ggcacgttgg tataacctgg    2040
ccgtctcaga gagcatcgaa aacctcagtc tggctcccct cagtcgtgtc tatcgctggc    2100
ccctggagag aatccagcaa ctcgccgcag atgtgaagtc cgaagcattc aacaaagaga    2160
tccatgccta caatatactg cacatatacc aggctaggaa accattaaga taagagcaaa    2220
aggcgaccac atccaggaac gcaaaacgaa aaggaggaaa actgctagcg caagtttatg    2280
tcacgctggc acacgcccag ccatcagaaa tctcaacagc gaaagttatg aaccgcatca    2340
accgagtatg aacgacaatt cgtccatcac acacccttcg gttcctctcg caggcccagc    2400
atggcgccct atcaacctgc tttacgacgt cgtatatact ggcgaagtat cctctctatc    2460
tactctggcg ctctagatac cgtgaagatg cagacaaaat tggccgagct cccttctcat    2520
aatcctcgac gccgcggggg tagtcgttat acgtgaaact atcatgacgc tcttgtcgtt    2580
accgctgcgc acctgggagg tataatagag tcgaattgcc ggtatcgtat actcatcgcg    2640
ggaatggaga tgatagagag ctatatcccc ggatcaagaa gttggccatg acggagtacg    2700
agaggagcat ggaaacaagc gacgagtagg tgagttatgt ggtgtggatc taggccccat    2760
atatattccc gagtcatgct aggtcccaca ctccggtttc tgcgacatat gcatgcaaca    2820
aagaatttgc ataaggcaat tgaaagctag tcacaaatag gagataaatt tatattgagc    2880
agaagcgaaa aggtttgact tctcgatcct tcatgtttac gttgcctaaa ctccaacccg    2940
tgattgatac tatatggatc ccatgtaccc gttccatgcc agcaaacaag caaatcccaa    3000
acgcctaaat ggctaggacc ggtccgtaag tctatgttta cagcttaaag gtggtcaaga    3060
gatgatccca tctcttactt gcgcagataa ttaccgtatc                          3100

<210> SEQ ID NO 2
<211> LENGTH: 1125
<212> TYPE: DNA
<213> ORGANISM: Aspergillus nidulans

<400> SEQUENCE: 2
atgtttgaga tgggcccggt gggaactcgt ctccccgcca tgacctctcc agcgcacaac      60
cactacagct accactctcc cacctccagc gacagaggcc ggtcaaggca gaactcggat     120
gccatggaca tccagtccat cactgaacga gagccggcga ccagatacgc ggttgcgggc     180
ggccctgcgc cctggaatcg caacgggtct ccgagcatga ccctatgta tagcaacaat     240 tccgagcgaa accagtttca tgaagagaac ggacgcacct accatggctt cgcagggga     300 atgtattttc ttccgtgcga tgagcaagaa caggatcgcc tcgacatctt ccataagcta     360
ttcacggtag cgcgggtatc ggagagtctg atctacgcgc ccatccaac caacggccgg     420 tttctggacc taggatgtgg aactggtatc tgggcgatcg aggtagcgaa caagtaccct     480
gatgcgtttg tcgctggtgt ggatttggct cctattcagc ctccgaacca cccgaagaac     540
tgcgagttct acgcgccctt cgacttcgaa gcgccatggg ccatggggga ggattcctgg     600
gatctaatcc atctgcagat gggttgcggt agtgtcatgg gctggccaaa cttgtatcga     660
```

```
aggatattcg cacatctccg tcccggtgcc tggtttgagc aggttgagat cgatttcgag    720
cctcgatgtg atgatcggtc actagatgga acggcattgc ggcattggta cgattgtctt    780
aaacaggcga cagcagagac catgcggcca atcgcccata gctcccgcga tacaataaaa    840
gacctgcagg acgctgggtt cacgagatc gaccatcaaa tagtgggact cccgctcaac     900
ccgtggcatc aggacgaaca cgagcggaag gtggcacgtt ggtataacct ggccgtctca    960
gagagcatcg aaaacctcag tctggctccc ttcagtcgtg tctatcgctg gcccctggga   1020
agaatccagc aactcgccgc agatgtgaag tccgaagcat caacaaaga gatccatgcc   1080 tacaatatac tgcacatata ccaggctagg aaaccattaa gataa                   1125
```

<210> SEQ ID NO 3
<211> LENGTH: 374
<212> TYPE: PRT
<213> ORGANISM: Aspergillus nidulans

<400> SEQUENCE: 3

```
Met Phe Glu Met Gly Pro Val Gly Thr Arg Leu Pro Ala Met Thr Ser
1               5                   10                  15

Pro Ala His Asn His Tyr Ser Tyr His Ser Pro Thr Ser Ser Asp Arg
            20                  25                  30

Gly Arg Ser Arg Gln Asn Ser Asp Ala Met Asp Ile Gln Ser Ile Thr
        35                  40                  45

Glu Arg Glu Pro Ala Thr Arg Tyr Ala Val Ala Gly Gly Pro Ala Pro
    50                  55                  60

Trp Asn Arg Asn Gly Ser Pro Ser Met Ser Pro Met Tyr Ser Asn Asn
65                  70                  75                  80

Ser Glu Arg Asn Gln Phe His Glu Glu Asn Gly Arg Thr Tyr His Gly
                85                  90                  95

Phe Gly Gly Arg Met Tyr Phe Leu Pro Cys Asp Glu Gln Glu Gln Asp
            100                 105                 110

Arg Leu Asp Ile Phe His Lys Leu Phe Thr Val Ala Arg Val Ser Glu
        115                 120                 125

Ser Leu Ile Tyr Ala Pro His Pro Thr Asn Gly Arg Phe Leu Asp Leu
    130                 135                 140

Gly Cys Gly Thr Gly Ile Trp Ala Ile Glu Val Ala Asn Lys Tyr Pro
145                 150                 155                 160

Asp Ala Phe Val Ala Gly Val Asp Leu Ala Pro Ile Gln Pro Pro Asn
                165                 170                 175

His Pro Lys Asn Cys Glu Phe Tyr Ala Pro Phe Asp Phe Glu Ala Pro
            180                 185                 190

Trp Ala Met Gly Glu Asp Ser Trp Asp Leu Ile His Leu Gln Met Gly
        195                 200                 205

Cys Gly Ser Val Met Gly Trp Pro Asn Leu Tyr Arg Arg Ile Phe Ala
    210                 215                 220

His Leu Arg Pro Gly Ala Trp Phe Glu Gln Val Glu Ile Asp Phe Glu
225                 230                 235                 240

Pro Arg Cys Asp Asp Arg Ser Leu Asp Gly Thr Ala Leu Arg His Trp
                245                 250                 255

Tyr Asp Cys Leu Lys Gln Ala Thr Ala Glu Thr Met Arg Pro Ile Ala
            260                 265                 270

His Ser Ser Arg Asp Thr Ile Lys Asp Leu Gln Asp Ala Gly Phe Thr
        275                 280                 285

Glu Ile Asp His Gln Ile Val Gly Leu Pro Leu Asn Pro Trp His Gln
```

-continued

```
            290             295             300

Asp Glu His Glu Arg Lys Val Ala Arg Trp Tyr Asn Leu Ala Val Ser
305                 310                 315                 320

Glu Ser Ile Glu Asn Leu Ser Leu Ala Pro Phe Ser Arg Val Tyr Arg
                325                 330                 335

Trp Pro Leu Glu Arg Ile Gln Gln Leu Ala Ala Asp Val Lys Ser Glu
            340                 345                 350

Ala Phe Asn Lys Glu Ile His Ala Tyr Asn Ile Leu His Ile Tyr Gln
                355                 360                 365

Ala Arg Lys Pro Leu Arg
    370

<210> SEQ ID NO 4
<211> LENGTH: 22
<212> TYPE: DNA
<213> ORGANISM: Aspergillus nidulans

<400> SEQUENCE: 4
atctaccttt ctgggctcct gg                                            22

<210> SEQ ID NO 5
<211> LENGTH: 22
<212> TYPE: DNA
<213> ORGANISM: Aspergillus nidulans

<400> SEQUENCE: 5
cgtgaagaac ttggcgttgt ag                                            22

<210> SEQ ID NO 6
<211> LENGTH: 28
<212> TYPE: DNA
<213> ORGANISM: Aspergillus nidulans

<400> SEQUENCE: 6
gacgagctcg tggaacagtg gaaggaac                                      28

<210> SEQ ID NO 7
<211> LENGTH: 27
<212> TYPE: DNA
<213> ORGANISM: Aspergillus nidulans

<400> SEQUENCE: 7
gcgaagctta tgaaccgcat caaccga                                       27

<210> SEQ ID NO 8
<211> LENGTH: 28
<212> TYPE: DNA
<213> ORGANISM: Aspergillus nidulans

<400> SEQUENCE: 8
gctgtgaagc tttgtaccct gtttcgcc                                      28

<210> SEQ ID NO 9
<211> LENGTH: 28
<212> TYPE: DNA
<213> ORGANISM: Aspergillus nidulans

<400> SEQUENCE: 9
gatttgaagc tttgctggca tggaacgg                                      28

<210> SEQ ID NO 10
```

<211> LENGTH: 31
<212> TYPE: DNA
<213> ORGANISM: Aspergillus nidulans

<400> SEQUENCE: 10
atgctgaagc ttggaaactg ggaaaggggt c                          31

<210> SEQ ID NO 11
<211> LENGTH: 31
<212> TYPE: DNA
<213> ORGANISM: Aspergillus nidulans

<400> SEQUENCE: 11
tgacgaattc tcttaatggt ttcctagcct g                          31

<210> SEQ ID NO 12
<211> LENGTH: 28
<212> TYPE: DNA
<213> ORGANISM: Aspergillus nidulans

<400> SEQUENCE: 12
tgcggaattc atgagcaagg gcgaggaa                              28

<210> SEQ ID NO 13
<211> LENGTH: 32
<212> TYPE: DNA
<213> ORGANISM: Aspergillus nidulans

<400> SEQUENCE: 13
ggatgcctcg agtttgtaca gctcgtccat gc                         32

<210> SEQ ID NO 14
<211> LENGTH: 32
<212> TYPE: DNA
<213> ORGANISM: Aspergillus nidulans

<400> SEQUENCE: 14
aagcagctcg agtaagagca aaaggcgacc ac                         32

<210> SEQ ID NO 15
<211> LENGTH: 32
<212> TYPE: DNA
<213> ORGANISM: Aspergillus nidulans

<400> SEQUENCE: 15
ctagcgaagc ttgccaccaa tgagcaaggg cg                         32

<210> SEQ ID NO 16
<211> LENGTH: 30
<212> TYPE: DNA
<213> ORGANISM: Aspergillus nidulans

<400> SEQUENCE: 16
cggcgaattc cttgtacagc tcgtccatgc                            30

<210> SEQ ID NO 17
<211> LENGTH: 31
<212> TYPE: DNA
<213> ORGANISM: Aspergillus nidulans

<400> SEQUENCE: 17
tttggaattc gtttcgccgc tgatgtttga g                          31

-continued

```
<210> SEQ ID NO 18
<211> LENGTH: 22
<212> TYPE: DNA
<213> ORGANISM: Aspergillus nidulans

<400> SEQUENCE: 18
gcgcacttct ttgttttccc ct                                               22

<210> SEQ ID NO 19
<211> LENGTH: 24
<212> TYPE: DNA
<213> ORGANISM: Aspergillus nidulans

<400> SEQUENCE: 19
ctcggaattc tttcttgagc ggcc                                             24

<210> SEQ ID NO 20
<211> LENGTH: 25
<212> TYPE: DNA
<213> ORGANISM: Aspergillus nidulans

<400> SEQUENCE: 20
taccaggatc caaaacctct cgcca                                            25

<210> SEQ ID NO 21
<211> LENGTH: 23
<212> TYPE: DNA
<213> ORGANISM: Aspergillus nidulans

<400> SEQUENCE: 21
catgacggta actaaggatt tgg                                              23
```

US 7,427,484 B2

GLOBAL REGULATOR OF SECONDARY METABOLITE BIOSYNTHESIS AND METHODS OF USE

CROSS-REFERENCE TO RELATED APPLICATIONS

This application is a divisional of U.S. patent application Ser. No. 10/668,696, issued as U.S. Pat. No. 7,053,204, filed Sep. 23, 2003 which claims the benefit of U.S. Provisional Application No. 60/413,073, filed on Sep. 24, 2002, both of which are incorporated by reference in their entirety for all purposes.

STATEMENT AS TO RIGHTS TO INVENTIONS MADE UNDER FEDERALLY SPONSORED RESEARCH AND DEVELOPMENT

This work was supported in part by a grant from the National Science Foundation NSF-0196233. The Government of the United States of America may have certain rights in this invention.

FIELD OF THE INVENTION

This invention relates generally to the field of secondary metabolite production in fungi. In particular, this invention is directed to a gene encoding a regulator of secondary metabolite biosynthesis and methods of using the same.

BACKGROUND OF THE INVENTION

Secondary metabolites display a broad range of useful antibiotic and immunosuppressant activities as well as less desirable phyto- and mycotoxic activities. (Demain, A., and Fang, A. (2000) The Natural Functions of Secondary Metabolites. In Advances in Biochemical Engineering/Biotechnology, T. Scheper, ed. (Berlin Heidelberg, Springer-Verlag), pp. 1-39). For example, penicillin and derivatives, produced by *Aspergillus, Cephalosporium* and *Penicillium* species are widely used antibiotics (Brakhage, A. A. (1998) Microbiol. Mol. Biol. Rev. 62, 547-585), lovastatin is a potent cholesterol lowering drug produced by *Aspergillus terreus* (Kennedy et al. (1999) Science 284, 1368-1372) and aflatoxins, produced by several *Aspergillus* species, are highly toxic carcinogens contaminating many crops (Hicks et al. (2002) Genetics and Biosynthesis of Aflatoxins and Sterigmatocystin. in The Mycota, Vol. XI, Kempken and Bennett, eds. (Spring-Verlag). The distribution of natural products is characteristically restricted to certain fungal taxa, particularly the *Ascomycetes*. Perhaps the greatest number of known secondary metabolites has been ascribed to the *Ascomycete* genus *Emericella* (asexual stage=*Aspergillus*). (reviewed in Brakhage, 1998 and Hicks et al., 2002 respectively).

Much of the current understanding of fungal secondary metabolite regulation arises from studies of the genetic model *Aspergillus nidulans*. This organism produces many natural products including sterigmatocystin ST (ST; the penultimate precursor to aflatoxin) (Hicks et al., 2002) and penicillin (Brakhage, 1998; Penalva et al. (1998) Trends Biotechnol. 16, 483-489) and has been used as a heterologous host to study the biosynthesis of other natural products including lovastatin (Kennedy et al., 1999). Critical advances in understanding of fungal secondary metabolism have been largely based on primary studies from *A. nidulans* and/or secondary studies in other fungi where researchers were able to exploit the knowledge gained from *A. nidulans* to their fungus of choice (Tag et al. (2000) Mol. Microbiol. 38, 658-665; Borgia et al. (1994) FEMS Microbiol. Lett. 122, 227-231; Shen et al. (1998) Genetics 148, 1031-1041). These advances include the discovery of a penicillin (Montenegro et al. (1992) J. Bacteriol. 174, 7063-7067) and ST biosynthetic gene cluster (Brown et al. (1996) Proc. Natl. Acad. Sci. USA 93, 1418-1422) and the establishment of a G-protein/cAMP/protein kinase A mediated growth pathway in *A. nidulans* regulating secondary metabolism production and sporulation (Hicks et al., 1997; Tag et al., 2000; Shimizu et al. (2001) Genetics 157, 591-600).

Through the use of *Aspergillus nidulans*, it is now apparent that structural genes required for most secondary metabolites are clustered (Keller et al. (1997) Fungal Genetics and Biology 21, 17-29), that the regulation of the clustered genes is largely dependent on pathway specific transcription factors (Fernandes et al. (1998) Mo. Microbiol 28, 1355-1365; Hohn et al (1999) Fungal Genet. Biol. 26, 224-235; Tsuji et al. (2000) Mol. Microbiol. 38, 940-954) and that G protein regulation of fungal secondary metabolism is likely to be a conserved phenomena (Tag et al., 2000) presumably transmitted through the pathway specific transcription factor.

The biosynthetic genes necessary for sterigmatocystin (ST) production in *A. nidulans* are clustered on a ca. 60-kb region on chromosome IV (Brown et al., 1996). The expression of these cluster genes (called stc genes) is regulated by the sixth gene in the cluster, aflR. aflR encodes a zinc binuclear cluster DNA binding protein which binds to AflR sites in stc promoters (Fernandes et al., 1998). ST is the penultimate precursor of aflatoxin (AF), which is produced by the related species *A. flavus* and *A. parasitieus*. AflR was first identified in *A. favus* (Payne et al. (1993) Appl. Environ Microbiol. 59, 156-162) and subsequently in *A. parasiticus* (Chang et al. (1993) Appl. Environ. Microbiol. 59, 3273-3279). AflR regulates the expression of the AF cluster genes in both *A. flavus* and *A. parasiticus* in a manner similar to the stc genes. aflR is not constitutively expressed in these three species and is regulated through a complex interaction with G protein/cAMP/protein kinase A signal transduction pathway also involved in asexual spore development (Hicks et al., 1997; Shimizu and Keller, 2001).

The discovery of G protein/cAMP/protein kinase A regulation of ST and other fungal secondary metabolites (Shimizu and Keller; 2001; Hicks et al., 2002; Tag et al., 2000) has been decidedly helpful in establishing a concept of global regulation of secondary metabolism. However, currently available signal transduction mutants have pleiotrophic effects on the fungi, the most notable effect being the gross impact on spore production and vegetative hyphal growth (Hicks et al., 1997; Tag et al., 2000; Shimizu and Keller, 2001; Adams et al. (1998) Curr. Opin. Microbiol. 1, 674-677). Thus, currently available signal transduction mutants are so impaired as to fungal development that further elucidation of genes specific for regulation of secondary metabolite gene clusters is difficult.

Studies of bacteria have only recently identified unique proteins whose primary function appears to be directed to regulation of multiple groups of secondary metabolism genes. These include AfsR, a transcriptional factor with ATPase activity regulating the production of actinorhodin, undecylprodigiosin and calcium-dependent antibiotic in *Streptomyces coelicolor* (Lee et al. (2002) Mol. Microbiol. 43, 1413-1430) and RsmA, a post transcriptional regulator of secondary metabolites and virulence factors in *Pseudomonas aeruginosa* (Pessi et al. (2001) J. Bacteriol. 183, 6676-6683). Similar proteins have not yet been identified in fungi but the existence of such in bacteria suggests the exciting possibility of global regulators of secondary metabolism in the Fungal Kingdom.

Although various similarities have been observed between secondary metabolite gene clusters in terms of cluster-specific regulatory elements, identification of regulatory elements providing global regulation of secondary metabolite gene clusters with little effect on sporulation and vegetative growth have not been reported. Such regulatory elements are extremely desirable because they would possess broad specificity for the activation and/or repression of entire families of secondary metabolite gene clusters while providing strains capable of otherwise normal or near-normal development and growth. Furthermore, identification of such regulatory elements would enable the increased production of secondary metabolites by providing improved strains of engineered organisms and also contribute to the broader understanding of molecular mechanisms by which secondary metabolites are produced.

SUMMARY OF THE INVENTION

The inventors describe and claim herein an archetypal global regulator of secondary metabolism in fungi, termed LaeA. Deletion of the gene encoding LaeA blocks sterigmatocystin (polyketide carcinogen), penicillin (non-ribosomal peptide antibiotic), lovastatin (polyketide antihypercholesterolemic agent) and mycelial pigment biosynthesis in *A. nidulans*, and gliotoxin (non-ribosomal peptide immunotoxin) and mycelial pigment biosynthesis in *A. fumigatus*. In contrast, over expression of laeA triggers increased penicillin production of 400-900% in *A. nidulans* and lovastatin product formation of 500-700% in *A. terreus*, respectively.

Thusly, the present invention provides an isolated polypeptide comprising an amino acid sequence selected from the group consisting of: (a) an amino acid sequence which is at least 85% identical to the LaeA amino acid sequence set forth in SEQ ID NO:3; (b) an amino acid sequence encoded by a nucleic acid comprising the laeA nucleotide sequence set forth in SEQ ID NO:2; and (c) an amino acid sequence encoded by a nucleic acid which specifically hybridizes under stringent conditions to either strand of a denatured, double-stranded nucleic acid comprising the laeA nucleotide sequence set forth in SEQ ID NO:2.

In one preferred embodiment, the isolated polypeptide according to the invention possesses secondary metabolite gene cluster regulating activity. In more preferred embodiments, the polypeptide possesses regulating activity for the lovastatin or penicillin biosynthesis gene cluster.

In certain embodiments, the polypeptide has protein methyltransferase activity. In yet other embodiments, the polypeptide comprises an amino acid sequence at least 95% identical to the complete LaeA amino acid sequence set forth in SEQ ID NO:3, or a fragment thereof. In a most preferred embodiment, the polypeptide is the LaeA amino acid sequence set forth in SEQ ID NO:3.

In yet another aspect, the present invention provides an isolated nucleic acid comprising a nucleotide sequence selected from the group consisting of: (a) an laeA nucleotide sequence set forth in SEQ ID NO:2; (b) a nucleotide sequence encoding the LaeA amino acid sequence set forth in SEQ ID NO:3; and (c) a nucleotide sequence which specifically hybridizes under stringent conditions to either strand of a denatured, double-stranded laeA nucleic acid having a nucleotide sequence set forth in SEQ ID NO:2.

The invention further provides expression vectors including an isolated nucleic acid as described and claimed herein which is in operative association with one or more regulatory elements. As well, transformed host cells or organisms comprising an isolated nucleic acid as described and claimed herein are further contemplated by the invention. In preferred embodiments, transformed host cells or organisms produce secondary metabolites in increased amounts relative to untransformed cells or organisms. The increased secondary metabolite production is preferably at least two fold greater than that of untransformed cells or organisms.

Also provided by the invention are methods of preparing an isolated polypeptide comprising LaeA or fragments thereof. Such methods include the step of culturing a transformed host cell or organism as described and claimed herein under conditions conducive to expression of the polypeptide, and recovering the expressed polypeptide from the cell or organism in isolated form.

The invention is also directed to methods of detecting a nucleic acid encoding an LaeA amino acid sequence set forth in SEQ ID NO:3 in a biological sample comprising the steps of: (a) hybridizing a complement of a nucleotide sequence which encodes an LaeA amino acid sequence as set forth in SEQ ID NO:3 to a nucleic acid material of a biological sample thereby forming a hybridization complex; and (b) detecting the hybridization complex wherein the presence of the complex correlates with the presence of a nucleic acid encoding an LaeA amino acid sequence set forth in SEQ ID NO:3.

The present invention further encompasses methods of increasing the amount of a secondary metabolite produced in a cell or organism. Such methods include steps of: (a) obtaining a cell or an organism capable of biosynthesizing a secondary metabolite; (b) transforming the cell or organism with an nucleic acid encoding an LaeA polypeptide capable of regulating biosynthesis of the secondary metabolite; and (c) culturing the transformed cell or organism so that an increase in production of the secondary metabolite occurs in the transformed cell or organism as compared to a non-transformed cell or organism.

Preferably, methods of increasing the amount of a secondary metabolite as described and claimed herein are practiced in an *Aspergillus* species. Even more preferably, the *Aspergillus* species is *A. nidulans* or *A. terreus*. As well, preferred secondary metabolites increased by the methods are lovastatin or penicillin.

The invention also provides methods of decreasing the production of a secondary metabolite in a transformed cell or organism. Such methods include the steps of: (a) obtaining a transformed cell or organism capable of biosynthesizing a secondary metabolite, the transformed cell or organism having a defective laeA gene wherein the defective laeA gene is no longer biologically active and expression of secondary metabolite gene clusters is reduced; and (b) culturing the transformed cell or organism so that a decrease in production of the secondary metabolite occurs in the transformed cell or organism as compared to a non-transformed cell or organism.

In yet another embodiment, the present invention encompasses methods of producing an isolated secondary metabolite. These methods include steps of: (a) obtaining a cell or an organism capable of biosynthesizing a secondary metabolite; (b) transforming the cell or organism with a nucleic acid encoding an LaeA polypeptide capable of regulating biosynthesis of the secondary metabolite; (c) culturing the transformed cell or organism under conditions conducive to increasing production of the secondary metabolite in the transformed cell or organism as compared to a non-transformed cell or organism; and (d) recovering the secondary metabolite from the transformed cell or organism in an isolated form.

Finally, the invention provides methods for identifying yet undiscovered secondary metabolite biosynthesis gene clusters in a variety of fungi based on the nucleic acids and transformed cells disclosed herein. Such methods are preferably carried out in a microarray format.

Other objects, features and advantages of the present invention will become apparent after review of the specification, claims and drawings.

BRIEF DESCRIPTION OF THE DRAWINGS

FIG. 1. a, Schematic of laeA gene. Although LaeA contains the exact SAM motif found in histone methyltransferases (HMTases) and arginine methyltransferases (PRMTs), it lacks other conserved domains (e.g. SET domain, a double E loop) typically found in these proteins. In addition, likely HMTase and PRMT candidates are found in the *Aspergillus* database ($1e^{-42}$; $1e^{-94}$). Therefore LaeA appears to be a unique protein methyltransferase. b, Amino acid comparison of *A. nidulans, A. fumigatus, Neurospora crassa, Magnaporthe grisea, Coccidioides immitis* and *Fusarium sporotrichioides* LaeA proteins showing conserved protein methyltransferase s-adenosylmethionine binding site in red. c, Loss of protein methylation in soluble nuclear extract from the ΔlaeA strain.

FIG. 2. a, Asexual sporulation (top) and mycelial pigmentation (bottom) patterns of *A. nidulans* WT (RDIT2.3) and ΔlaeA (RJW46.4) strains after 5 days cultivation on glucose minimal medium (GMM). *A. fumigatus* ΔlaeA presented a similar loss of mycelial pigmentation (also see FIG. 5). b, Thin layer chromatography analysis of organic solvent extracts of RDIT2.3 and RJW46.4 after 5 days cultivation on solid GMM. c, Thin layer chromatography analysis of organic solvent extracts of *A. fumigatus* AF293 (WT) and TJW54.2 (ΔlaeA) grown in liquid shaking GMM for 3 days. Experiment was triplicated. ST=sterigmatocystin and Std=gliotoxin standard.

DETAILED DESCRIPTION OF THE INVENTION

I. In General

Figure 3:
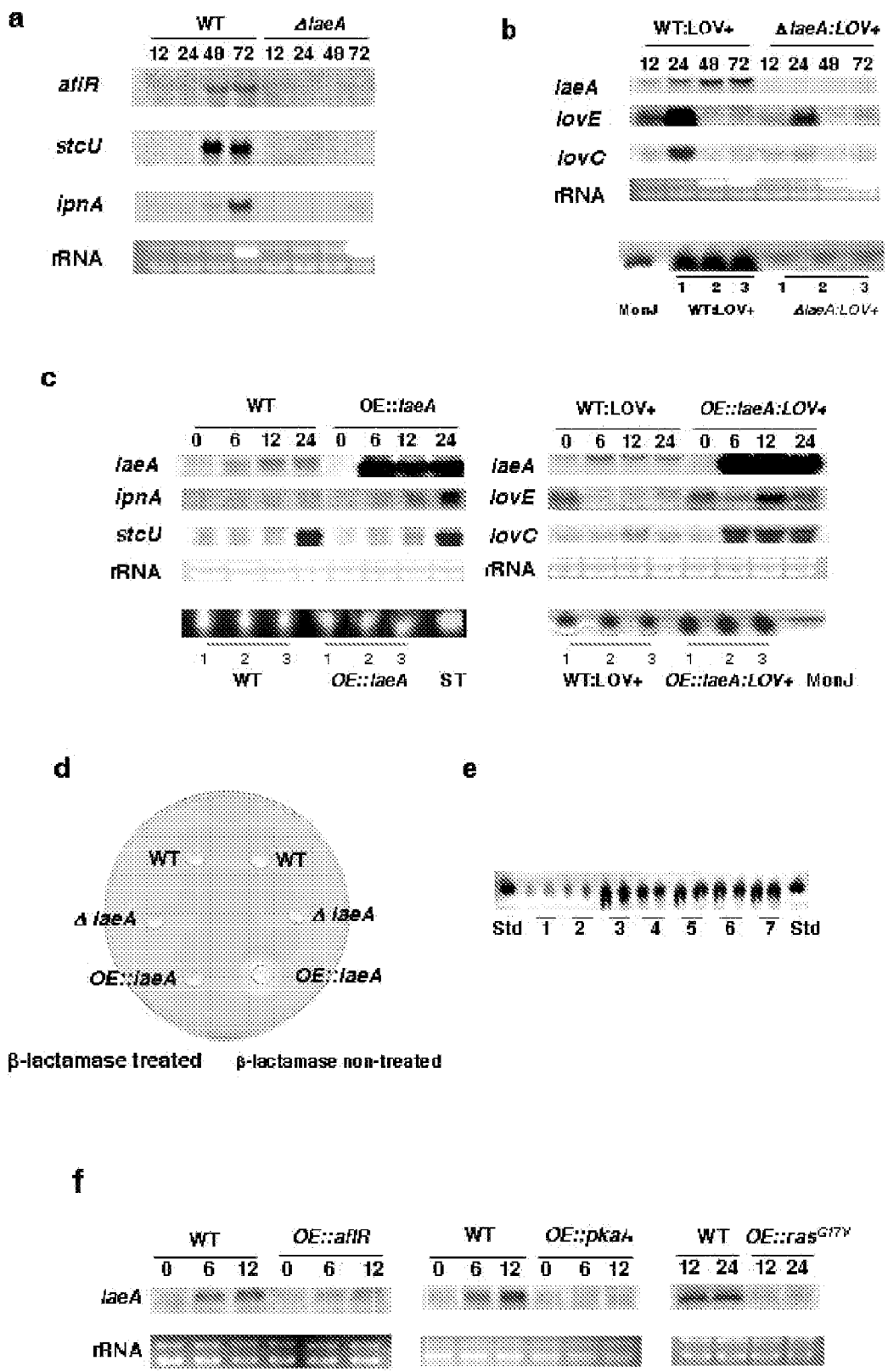
FIG. 3. laeA regulation of secondary metabolism. a, aflR, stcU and ipnA gene expression in *A. nidulans* WT (RDIT2.3) and ΔlaeA (RJW46.4) grown in liquid shaking GMM for 12 h, 24 h, 48 h and 72 h at 37° C. Ethidium bromide stained rRNA is indicated for loading. b, laeA, lovE and lovC gene expression in *A. nidulans* WT;lov+(RJW51) and ΔlaeA;lov+ (RJW53) strains grown in liquid shaking GMM for 12 h, 24 h, 48 h and 72 h at 37° C. Ethidium bromide stained rRNA is indicated for loading. MONJ was extracted from WT; lov+ (RJW51) and ΔlaeA; lov+(RJW53) *A. nidulans* strains grown in liquid shaking GMM for 3 days. Experiment was triplicated. c, laeA, ipnA, stcU, lovE and lovC gene expression, and ST and MONJ extraction in *A. nidulans* WT (RDIT2.3) and OE::laeA (RJW47.3), and WT:lov+(RJW51) and OE:: laeA;lov+(RJW52) grown in liquid shaking GMM for 14 h at 37° C., and then transferred to liquid shaking threonine minimal media for induction of laeA expression. Time points were 0h, 6 h, 12 h and 24 h after transfer. ST and MONJ extracts from *A. nidulans* WT (RDIT2.3) and OE::laeA (RJW47.3), and WT; lov+(RJW51) and OE::laeA; lov+(RJW52) grown in liquid shaking GMM for 14 h at 37° C., and then transferred to liquid shaking threonine minimal media for 24 h after switch ST=ST standard. MONJ standard was extracted from *A. nidulans* strain WMH1739. Experiment was triplicated. d, Penicillin bioassay. Wild type (FGSC26), ΔlaeA (RJW40.4) and OE::laeA (RJW44.2) were grown in liquid shaking GMM for 14 h at 37° C., and then transferred to lactose minimal medium amended with 30 mM cyclopentanone for induction of laeA for 24 h at 37° C. e, Lovastatin production in *A. terreus* in laeA over expression strains. Wild type (ATCC20542, lane 1), TJW58.9 (hygB resistance gene containing transformant as a control, lane 2) and OE::laeA strains containing hygB (TJW58.2, TJW58.4, TJW58.7, TJW58.8 and TJW58.14 are lanes 3, 4, 5, 6 and 7, respectively) were grown in liquid shaking GMM for 18 h at 32° C., and then transferred to lactose minimal medium with 30 mM cyclopentanone for induction of laeA for 36 h at 32° C. Std=lovastatin standard. Experiment was duplicated. f, Regulation of laeA. Effects of over expression of aflR, pkaA and $ras^{G17V}$ on laeA expression. WT (RKIS1), OE::aflR (TJH34.10), OE::pkaA (TKIS20.1) and OE::$ras^{G17V}$ (RKIS28.5) were grown in liquid shaking GMM for 14 h at 37° C., and then transferred to threonine minimal medium. Time points were 0h, 6 h, 12 h or 24 h after transfer.

Before the present polypeptides, nucleic acids, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a cell" includes a plurality of such cells, reference to the "vector" is a reference to one or more vectors and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the polypeptides, polynucleotides, cell lines, vectors, and methodologies which are reported in the publications which might be used in connection with the invention. Nothing herein is to be construed as an admission that the invention is not entitled to antedate such disclosure by virtue of prior invention.

The practice of the present invention will employ, unless otherwise indicated, conventional techniques of molecular biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Cell Culture and Somatic Cell Genetics of Plants, Vol. 1 (I. K. Vasil, ed. 1984); R. V. Stanier, J. L. Ingraham, M. L. Wheelis, and P. R. Painter, The Microbial World, (1986) 5th Ed. Prentice-Hall.

II. Definitions

"LaeA", as used herein, refers to the amino acid sequences of the LaeA protein obtained from *Aspergillus nidulans*. In addition, LaeA shall also refer to the amino acid sequences of LaeA obtained from any species (i.e., orthologs), particularly fungi (e.g. other strains and/or species of *Aspergillus*, and the like), from any source whether natural, synthetic, semi-synthetic, or recombinant. The term encompasses proteins encoded by nucleotide sequences representing allelic variants as well as those containing single nucleotide polymorphisms (SNPs).

"laeA", as used herein, refers to the nucleotide sequences of the laeA gene obtained from *Aspergillus nidulans*. In addition, laeA shall also refer to the nucleotide sequences of the laeA gene obtained from any species, particularly fungi (e.g. other strains and/or species of *Aspergillus*, and the like), from any source whether natural, synthetic, semi-synthetic, or recombinant. The term encompasses allelic variants and single nucleotide polymorphisms (SNPs).

"SEQ ID NO:1" refers to a nucleotide sequence from genomic DNA isolated from *A. nidulans* which is 3100 nucleotides in length and encompasses coding sequence for the LaeA protein as well as upstream and downstream genomic DNA sequences. SEQ ID NO:1 is set forth in its entirety in the Sequence Listing. The LaeA coding sequence extends from a start codon at nt 959 to a stop codon at nt 2213 with a single intron interrupting the coding sequence from nt 1195-1323.

"SEQ ID NO:2", set forth in its entirety in the Sequence Listing, refers to cDNA isolated from *A. nidulans* which is 1125 nucleotides in length and encompasses the nucleotide sequence encoding the LaeA protein.

"SEQ ID NO:3" refers to an amino acid sequence encoding the LaeA protein of 374 amino acids in length as isolated from *A. nidulans* and set forth in the Sequence Listing.

An "allele" or "allelic sequence", as used herein, is an alternative form of the gene encoding LaeA. Alleles may result from at least one mutation in the nucleic acid sequence and may result in altered mRNAs or polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding LaeA, as used herein, include those with deletions, insertions, or substitutions of different nucleotides resulting in a polynucleotide that encodes the same or a functionally equivalent protein to LaeA. Included within this definition are polymorphisms which may or may not be readily detectable using a particular oligonucleotide probe of the polynucleotide encoding LaeA, and improper or unexpected hybridization to alleles, with a locus other than the normal chromosomal locus for the polynucleotide sequence encoding LaeA. The encoded protein may also be "altered" and contain deletions, insertions, or substitutions of amino acid residues which produce a silent change and result in a functionally equivalent LaeA. Deliberate amino acid substitutions may be made on the basis of similarity in polarity, charge, solubility, hydrophobicity, hydrophilicity, and/or the amphipathic nature of the residues as long as the biological or immunological activity of LaeA is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine, glycine and alanine, asparagine and glutamine, serine and threonine, and phenylalanine and tyrosine.

"Amino acid sequence", as used herein, refers to an oligopeptide, peptide, polypeptide, or protein sequence, and fragment thereof. Where "amino acid sequence" is recited herein to refer to a particular amino acid sequence (e.g., the amino acid sequence set forth in SEQ ID NO:3), "amino acid sequence", and like terms, are not meant to limit the amino acid sequence to the complete amino acid sequence referenced but shall be understood to include fragments of the complete amino acid sequence. The term shall further encompass synthetic molecules as well as those occurring naturally. The term "portion" or "fragment", as used herein, with regard to an amino acid sequence (as in "a fragment of SEQ ID NO:3"), specifically refers to segments of that amino acid sequence which are not naturally occurring as fragments and would not be found in the natural state. The segments may range in size from five amino acid residues to the entire amino acid sequence minus one amino acid. Thus, a polypeptide "comprising at least a portion of the amino acid sequence of SEQ ID NO:3" or "including an amino acid sequence as set forth in SEQ ID NO:3 or fragments thereof" encompasses the full-length LaeA amino acid sequences and segments thereof.

"Amplification", as used herein, refers to the production of additional copies of a nucleic acid sequence and is generally carried out using polymerase chain reaction (PCR) technologies well known in the art (Dieffenbach, C. W. and G. S. Dveksler (1995) PCR Primer, a Laboratory Manual, Cold Spring Harbor Press, Plainview, N.Y.).

The term "antisense", as used herein, refers to any composition containing nucleotide sequences which are complementary to a specific DNA or RNA sequence. The term "antisense strand" is used in reference to a nucleic acid strand that is complementary to the "sense" strand. Antisense molecules include peptide nucleic acids and may be produced by any method including synthesis or transcription. Once introduced into a cell, the complementary nucleotides combine with natural sequences produced by the cell to form duplexes and block either transcription or translation. The designation "negative" is sometimes used in reference to the antisense strand, and "positive" is sometimes used in reference to the sense strand.

The term "biologically active", as used herein, refers to a protein, polypeptide, amino acid sequence, or nucleotide sequence encoding a product having structural, regulatory, or biochemical functions of a naturally occurring molecule. Preferably, a biologically active fragment of LaeA will have the secondary metabolite gene cluster regulatory capabilities of a naturally occurring LaeA molecule disclosed herein.

The terms "complementary" or "complementarity", as used herein, refer to the natural binding of polynucleotides under permissive salt and temperature conditions by base-pairing. For example, the sequence "A-G-T" binds to the complementary sequence "T-C-A". Complementary between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands and in the design and use of PNA molecules.

A "composition comprising a given polynucleotide sequence", as used herein, refers broadly to any composition containing the given polynucleotide sequence. Compositions comprising polynucleotide sequences encoding LaeA (SEQ ID NO:1 or 2) or fragments thereof, may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS) and other components (e.g., Denhardt's solution, dry milk, salmon sperm DNA, etc.).

The term "correlates with expression of a polynucleotide", as used herein, indicates that the detection of the presence of ribonucleic acid that is similar to SEQ ID NO:2 by northern analysis or equivalent analysis is indicative of the presence of mRNA encoding LaeA in a sample and thereby correlates with expression of the transcript from the polynucleotide encoding the protein.

A "deletion", as used herein, refers to a change in the amino acid or nucleotide sequence and results in the absence of one or more amino acid residues or nucleotides.

The term "derivative", as used herein, refers to the chemical modification of a nucleic acid encoding or complementary to LaeA or the encoded LaeA protein itself. Such modifications include, for example, replacement of hydrogen by an alkyl, acyl, or amino group. A nucleic acid derivative encodes a polypeptide which retains the biological or immunological function of the natural molecule. A derivative polypeptide is one which is modified by glycosylation, or any similar process which retains the biological function of the polypeptide from which it was derived.

The term "homology", as used herein, refers to sequence similarity between two peptides or between two nucleic acid molecules. Homology may be determined by comparing a postion in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. A partially complementary sequence that at least partially inhibits an identical sequence from hybridizing to a target nucleic acid is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or hybridization probe will compete for and inhibit the binding of a completely homologous sequence to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementary (e.g., less than about 30% identity). In the absence of non-specific binding, the probe will not hybridize to the second non-complementary target sequence. In the art, "identity" means the degree of sequence relatedness between polypeptide or polynucleotide sequences, as the case may be, as determined by the match between strings of such sequences. "Identity" and "homology" can be readily calculated by known methods, including but not limited to those described in (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48: 1073 (1988). Preferred methods to determine identity are designed to give the largest match between the sequences tested. Methods to determine identity and homology are codified in publicly available computer programs. Preferred computer program methods to determine identity and homology between two sequences include, but are not limited to, the GCG program package (Devereux, J., et al., Nucleic Acids Research 12(1): 387 (1984)), BLASTP, BLASTN, and FASTA (Atschul, S. F. et al., J. Molec. Biol. 215: 403-410 (1990). The BLAST X program is publicly available from NCBI and other sources (BLAST Manual, Altschul, S., et al, NCBI NLM NIH Bethesda, Md. 20894; Altschul, S., et al., J. Mol. Biol. 215: 403-410 (1990). The well known Smith Waterman algorithm may also be used to determine identity.

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., C₀t or R₀t analysis) or between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

An "insertion" or "addition", as used herein, refers to a change in an amino acid or nucleotide sequence resulting in the addition of one or more amino acid residues or nucleotides, respectively, as compared to the naturally occurring molecule.

"Isolated" or "purified" or "isolated and purified" means altered "by the hand of man" from its natural state, i.e., if it occurs in nature, it has been changed or removed from its original environment, or both. For example, a polynucleotide or a polypeptide naturally present in a living organism is not "isolated," but the same polynucleotide or polypeptide separated from the coexisting materials of its natural state is "isolated", as the term is employed herein. Moreover, a polynucleotide or polypeptide that is introduced into an organism by transformation, genetic manipulation or by any other recombinant method is "isolated" even if it is still present in said organism, which organism may be living or non-living. As so defined, "isolated nucleic acid" or "isolated polynucleotide" includes nucleic acids integrated into a host cell chromosome at a heterologous site, recombinant fusions of a native fragment to a heterologous sequence, recombinant vectors present as episomes or as integrated into a host cell chromosome. As used herein, the term "substantially purified", refers to nucleic or amino acid sequences that are removed from their natural environment, isolated or separated, and are at least 60% free, preferably 75% free, and most preferably 90% free from other components with which they are naturally associated. As used herein, an isolated nucleic acid "encodes" a reference polypeptide when at least a portion of the nucleic acid, or its complement, can be directly translated to provide the amino acid sequence of the reference polypeptide, or when the isolated nucleic acid can be used, alone or as part of an expression vector, to express the reference polypeptide in vitro, in a prokaryotic host cell, or in a eukaryotic host cell.

As used herein, the term "exon" refers to a nucleic acid sequence found in genomic DNA that is bioinformatically predicted and/or experimentally confirmed to contribute contiguous sequence to a mature mRNA transcript.

As used herein, the phrase "open reading frame" and the equivalent acronym "ORF" refer to that portion of a transcript-derived nucleic acid that can be translated in its entirety into a sequence of contiguous amino acids. As so defined, an ORF has length, measured in nucleotides, exactly divisible by 3. As so defined, an ORF need not encode the entirety of a natural protein.

The term "microarray" refers to an ordered arrangement of hybridizable array elements. The array elements are arranged so that there are preferably at least one or more different array elements, more preferably at least 100 array elements, and most preferably at least 1,000 array elements, on a 1 cm² substrate surface. The maximum number of array elements is unlimited, but is at least 100,000 array elements. Furthermore, the hybridization signal from each of the array elements is individually distinguishable. In a preferred embodiment, the array elements comprise polynucleotide representative of fungal-derived polynucleotide sequences.

The term "modulate", as used herein, refers to a change in the activity of LaeA. For example, modulation may cause an increase or a decrease in protein activity, binding characteristics, or any other biological, functional or immunological properties of LaeA.

"Nucleic acid sequence" or "nucleotide sequence" or "polynucleotide sequence", as used herein, refers to an oligonucleotide, nucleotide, or polynucleotide, and fragments thereof, and to DNA or RNA of genomic or synthetic origin which may be single- or double-stranded, and represent the sense or antisense strand. Where "nucleic acid sequence" or "nucleotide sequence" or "polynucleotide sequence" is recited herein to refer to a particular nucleotide sequence (e.g., the nucleotide sequence set forth in SEQ ID NO:2), "nucleotide sequence", and like terms, are not meant to limit the nucleotide sequence to the complete nucleotide sequence referenced but shall be understood to include fragments of the complete nucleotide sequence. In this context, the term "fragment" may be used to specifically refer to those nucleic acid sequences which are not naturally occurring as fragments and would not be found in the natural state. Generally, such fragments are equal to or greater than 15 nucleotides in length, and most preferably includes fragments that are at least 60 nucleotides in length. Such fragments find utility as, for example, probes useful in the detection of nucleotide sequences encoding LaeA.

The term "sample", as used herein, is used in its broadest sense. A biological sample suspected of containing nucleic acid encoding LaeA, or fragments thereof, or LaeA itself may comprise a bodily fluid, extract from a cell, chromosome, organelle, or membrane isolated from a cell, a cell, genomic DNA, RNA, or cDNA (in solution or bound to a solid support, a tissue, a tissue print, and the like).

A "substitution", as used herein, refers to the replacement of one or more amino acids or nucleotides by different amino acids or nucleotides, respectively. The term "conservative substitution" is used in reference to proteins or peptides to reflect amino acid substitutions that do not substantially alter the activity (specificity or binding affinity) of the molecule. Typically conservative amino acid substitutions involve substitution one amino acid for another amino acid with similar chemical properties (e.g. charge or hydrophobicity). The following six groups each contain amino acids that are typical conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W).

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

A "variant" of LaeA, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Analogous minor variations may also include amino acid deletions or insertions, or both. Guidance in determining which amino acid residues may be substituted, inserted, or deleted without abolishing biological or immunological activity may be found using computer programs well known in the art, for example, DNASTAR software.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The term also includes variations on the traditional peptide linkage joining the amino acids making up the polypeptide. Where the terms are recited herein to refer to a polypeptide, peptide or protein of a naturally occurring protein molecule, the terms are not meant to limit the polypeptide, peptide or protein to the complete, native amino acid sequence associated with the recited protein molecule but shall be understood to include fragments of the complete polypeptide. The term "portion" or "fragment", as used herein, with regard to a protein or polypeptide (as in "a fragment of the LaeA polypeptide") refers to segments of that polypeptide which are not naturally occurring as fragments in nature. The segments may range in size from five amino acid residues to the entire amino acid sequence minus one amino acid. Thus, a polypeptide "as set forth in SEQ ID NO:3 or a fragment thereof" encompasses the full-length amino acid sequence set forth in SEQ ID NO:3 as well as segments thereof. Fragments of LaeA preferably are biologically active as defined herein.

The terms "nucleic acid" or "oligonucleotide" or "polynucleotide" or grammatical equivalents herein refer to at least two nucleotides covalently linked together. A nucleic acid of the present invention is preferably single-stranded or double stranded and will generally contain phosphodiester bonds, although in some cases, as outlined below, nucleic acid analogs are included that may have alternate backbones, comprising, for example, phosphoramide (Beaucage et al. (1993) *Tetrahedron* 49:1925) and references therein; Letsinger (1970) *J. Org. Chem*. 35:3800; Sprinzl et al. (1977) *Eur. J. Biochem*. 81: 579; Letsinger et al. (1986) *Nucl. Acids Res*. 14: 3487; Sawai et al. (1984) *Chem. Lett*. 805, Letsinger et al. (1988) *J. Am. Chem. Soc*. 110: 4470; and Pauwels et al. (1986) *Chemica Scripta* 26: 141 9), phosphorothioate (Mag et al. (1991) *Nucleic Acids Res*. 19:1437; and U.S. Pat. No. 5,644, 048), phosphorodithioate (Briu et al. (1989) *J. Am Chem. Soc*. 111 :2321, O-methylphophoroamidite linkages (see Eckstein, *Oligonucleotides and Analogues: A Practical Approach*, Oxford University Press), and peptide nucleic acid backbones and linkages (see Egholm (1992) *J. Am. Chem. Soc*. 114:1895; Meieretal. (1992) *Chem. Int. Ed. Engl*. 31: 1008; Nielsen (1993) *Nature*, 365: 566; Carlsson et al. (1996) *Nature* 380: 207). Other analog nucleic acids include those with positive backbones (Denpcy et al. (1995) *Proc. Natl. Acad. Sci*. USA 92: 6097; non-ionic backbones (U.S. Pat. Nos. 5,386,023, 5,637,684, 5,602,240, 5,216,141 and 4,469, 863; Angew. (1991) Chem. Intl. Ed. English 30: 423; Letsinger et al. (1988) *J. Am. Chem. Soc*. 110:4470; Letsinger et al. (1994) *Nucleoside & Nucleotide* 13:1597; Chapters 2 and 3, ASC Symposium Series 580, "Carbohydrate Modifications in Antisense Research", Ed. Y. S. Sanghui and P. Dan Cook; Mesmaeker et al. (1994), *Bioorganic & Medicinal Chem. Lett*. 4: 395; Jeffs et al. (1994) *J. Biomolecular NMR* 34:17; *Tetrahedron Lett*. 37:743 (1996) and non-ribose backbones, including those described in U.S. Pat. Nos. 5,235,033 and 5,034,506, and Chapters 6 and 7, ASC Symposium Series 580, *Carbohydrate Modifications in Antisense Research*, Ed. Y. S. Sanghui and P. Dan Cook. Nucleic acids containing one or more carbocyclic sugars are also included within the definition of nucleic acids (see Jenkins et al. (1995), *Chem. Soc. Rev. pp* 169-176). Several nucleic acid analogs are described in Rawls, C & E News Jun. 2, 1997 page 35. These modifications of the ribose-phosphate backbone may be done to facilitate the addition of additional moieties such as labels, or to increase the stability and half-life of such molecules in physiological environments. As used herein, oligonucleotide is substantially equivalent to the terms "amplimers", "primers", "oligomers", and "probes", as commonly defined in the art.

The term "heterologous" as it relates to nucleic acid sequences such as coding sequences and control sequences, denotes sequences that are not normally associated with a region of a recombinant construct, and/or are not normally associated with a particular cell. Thus, a "heterologous" region of a nucleic acid construct is an identifiable segment of nucleic acid within or attached to another nucleic acid molecule that is not found in association with the other molecule in nature. For example, a heterologous region of a construct could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, a host cell transformed with a construct which is not normally present in the host cell would be considered heterologous for purposes of this invention.

A "coding sequence" or a sequence which "encodes" a particular polypeptide (e.g. a methyltransferase, etc.), is a nucleic acid sequence which is ultimately transcribed and/or translated into that polypeptide in vitro and/or in vivo when placed under the control of appropriate regulatory sequences. In certain embodiments, the boundaries of the coding sequence are determined by a start codon at the 5' (amino) terminus and a translation stop codon at the 3' (carboxy) terminus. A coding sequence can include, but is not limited to, cDNA from procaryotic or eucaryotic mRNA, genomic DNA sequences from procaryotic or eucaryotic DNA, and even synthetic DNA sequences. In preferred embodiments, a transcription termination sequence will usually be located 3' to the coding sequence.

The term "ortholog" refers to genes or proteins which are homologs via speciation, e.g., closely related and assumed to have common descent based on structural and functional considerations. Orthologous proteins function as recognizably the same activity in different species.

Expression "control sequences" or "regulatory elements" refers collectively to promoter sequences, ribosome binding sites, polyadenylation signals, transcription termination sequences, upstream regulatory domains, enhancers, and the like, which collectively provide for the transcription and translation of a coding sequence in a host cell. Not all of these control sequences need always be present in a recombinant vector so long as the desired gene is capable of being transcribed and translated.

"Recombination" refers to the reassortment of sections of DNA or RNA sequences between two DNA or RNA molecules. "Homologous recombination" occurs between two DNA molecules which hybridize by virtue of homologous or complementary nucleotide sequences present in each DNA molecule.

The terms "stringent conditions" or "hybridization under stringent conditions" refers to conditions under which a probe will hybridize preferentially to its target subsequence, and to a lesser extent to, or not at all to, other sequences. "Stringent hybridization" and "stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen (1993) *Laboratory Techniques in Biochemistry and Molecular Biology—Hybridization with Nucleic Acid Probes part I chapter 2 Overview of principles of hybridization and the strategy of nucleic acid probe assays*, Elsevier, New York. Generally, highly stringent hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ for a particular probe.

An example of stringent hybridization conditions for hybridization of complementary nucleic acids which have more than 100 complementary residues on a filter in a Southern or northern blot is 50% formamide with 1 mg of heparin at 42° C., with the hybridization being carried out overnight. An example of highly stringent wash conditions is 0.15 M NaCl at 72° C. for about 15 minutes. An example of stringent wash conditions is a 0.2×SSC wash at 65° C. for 15 minutes (see, Sambrook et al. (1989) *Molecular Cloning—A Laboratory Manual* (2nd ed.) Vol. 1-3, Cold Spring Harbor Laboratory, Cold Spring Harbor Press, N.Y., for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. In general, a signal to noise ratio of 2× (or higher) than that observed for an unrelated probe in the particular hybridization assay indicates detection of a specific hybridization. Nucleic acids which do not hybridize to each other under stringent conditions are still substantially identical if the polypeptides which they encode are substantially identical. This occurs, e.g., when a copy of a nucleic acid is created using the maximum codon degeneracy permitted by the genetic code.

"Expression vectors" are defined herein as nucleic acid sequences that are direct the transcription of cloned copies of genes/cDNAs and/or the translation of their mRNAs in an appropriate host. Such vectors can be used to express genes or cDNAs in a variety of hosts such as bacteria, bluegreen algae, plant cells, insect cells and animal cells. Expression vectors include, but are not limited to, cloning vectors, modified cloning vectors, specifically designed plasmids or viruses. Specifically designed vectors allow the shuttling of DNA between hosts, such as bacteria-yeast or bacteria-animal cells. An appropriately constructed expression vector preferably contains: an origin of replication for autonomous replication in a host cell, a selectable marker, optionally one or more restriction enzyme sites, optionally one or more constitutive or inducible promoters. In preferred embodiments, an expression vector is a replicable DNA construct in which a DNA sequence encoding LaeA or a fragment thereof is operably linked to suitable control sequences capable of effecting the expression of the products in a suitable host. Control sequences include a transcriptional promoter, an optional operator sequence to control transcription and sequences which control the termination of transcription and translation, and so forth.

A "polymorphism" is a variation in the DNA sequence of some members of a species. A polymorphism is thus said to be "allelic," in that, due to the existence of the polymorphism, some members of a species may have the unmutated sequence (i.e. the original "allele") whereas other members may have a mutated sequence (i.e. the variant or mutant "allele"). In the simplest case, only one mutated sequence may exist, and the polymorphism is said to be diallelic. In the case of diallelic diploid organisms, three genotypes are possible. They can be homozygous for one allele, homozygous for the other allele or heterozygous. In the case of diallelic haploid organisms, they can have one allele or the other, thus only two genotypes are possible. The occurrence of alternative mutations can give rise to trialleleic, etc. polymorphisms. An allele may be referred to by the nucleotide(s) that comprise the mutation.

"Single nucleotide polymorphism" or "SNPs are defined by their characteristic attributes. A central attribute of such a polymorphism is that it contains a polymorphic site, "X," most preferably occupied by a single nucleotide, which is the site of the polymorphism's variation (Goelet and Knapp U.S. patent application Ser. No. 08/145,145). Methods of identifying SNPs are well known to those of skill in the art (see, e.g., U.S. Pat. No. 5,952,174).

Abbreviations used herein include aa, amino acid; MMG, minimal media glucose; MMT, minimal media threonine; OE, over expression; LB, Luria-Bertani; nt, nucleotide; ORF, open reading frame; PCR, polymerase chain reaction; PEG, polyethyleneglycol; R, resistant; WT, wild-type; and TS, temperature sensitive.

III. The Invention

The invention is based on the discovery of a new fungal gene and protein encoded thereby which regulates the activity of multiple secondary metabolite gene clusters in fungi. Appropriate expression of the gene, laeA, provides increased production of secondary metabolites in engineered cells. In particular, such a method of increasing secondary metabolite allows the production of improved yields of valuable products including, but not limited to, lovastatin and penicillin.

Nucleic acids encoding LaeA were first identified by the present inventors in a screen designed to decouple asexual sporulation from ST biosynthesis in a norsolorinic acid (NOR) accumulating strain of *A. nidulans*. Various mutants displaying a phenotype of normal sporulation combined with loss of ST production were genetically characterized and placed into two groups depending on genetic linkage to the ST cluster. The non-linked mutants were further characterized with regard to their ability to regulate aflR transcription. Several of these mutants were complemented by an *A. nidulans* cosmid library. The complementation of aflR subsequently yielded the gene, laeA, which appears to encode a novel protein methyltransferase. Upon functional characterization, the laeA gene was discovered to possess characteristics of a global, or universal, regulator of secondary metabolism that is required not only for ST biosynthesis and mycelial mat pigmentation but also for PN and LOV biosynthesis.

In one embodiment, the invention is directed to the polypeptide set forth in SEQ ID NO:3 (i.e., the mature polypeptide) as well as polypeptides and fragments, particularly those which have the biological activity of LaeA, and also those which have at least 85% identity over their length to a polypeptide of SEQ ID NO:3, and more preferably at least 90% identity over their length to a polypeptide of SEQ ID NO:3, and still more preferably at least 95% identity over their length to a polypeptide of SEQ ID NO:3.

A polypeptide fragment according to the invention is a polypeptide having an amino acid sequence that is entirely the same as part but not all of the amino acid sequence of the aforementioned polypeptides. LaeA polypeptide fragments may be "free-standing," or comprised within a larger polypeptide of which they form a part or region, most preferably as a single continuous region, a single larger polypeptide.

Preferred fragments include, for example, truncation polypeptides having a portion of an amino acid sequence of SEQ ID NO:3, or of variants thereof, such as a continuous series of residues that includes the amino terminus, or a continuous series of residues that includes the carboxyl terminus. Further preferred are fragments characterized by structural or functional attributes such as fragments that comprise catalytic domains, alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions.

Also preferred are biologically active fragments which are those fragments that mediate activities of LaeA, including those with a similar activity or an improved activity, or with a decreased undesirable activity. Particularly preferred fragments are those capable of global regulation of secondary metabolite biosynthesis. Also included are those fragments that are antigenic or immunogenic in an animal, especially in a human. Fragments of the polypeptides of the invention may be employed for producing the corresponding full-length polypeptide by peptide synthesis; therefore, these particular fragments may be employed as intermediates for producing the full-length polypeptides of the invention.

The present invention also encompasses nucleic acids which encode LaeA. Accordingly, any nucleic acid sequence which encodes the amino acid sequence of LaeA can be used to produce recombinant molecules which express LaeA. In a particular embodiment, the invention encompasses the nucleic acid comprising the nucleic acid sequence of SEQ ID NO:1 or SEQ ID NO:2.

It will be appreciated by those skilled in the art that as a result of the degeneracy of the genetic code, a multitude of nucleotide sequences encoding LaeA, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring LaeA, and all such variations are to be considered as being specifically disclosed.

Preferred embodiments of the invention are polynucleotides that are at least 70% identical over their entire length to a polynucleotide set out in SEQ ID NO:2, and polynucleotides that are complementary to the same. Alternatively, most highly preferred are polynucleotides that comprise a region that is at least 80% identical over its entire length to a polynucleotide set out in SEQ ID NO:2 and polynucleotides complementary thereto. In this regard, polynucleotides at least 90% identical over their entire length to the same are particularly preferred, and among these particularly preferred polynucleotides, those with at least 95% are especially preferred. Furthermore, those with at least 97% are highly preferred, and among these those with at least 98% and at least 99% are particularly highly preferred, with at least 99% being the more preferred.

Although nucleotide sequences which encode LaeA and its variants are preferably capable of hybridizing to the nucleotide sequence of the naturally occurring LaeA under appropriately selected conditions of stringency, it may be advantageous to produce nucleotide sequences encoding LaeA or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding LaeA and its derivatives without altering the encoded amino acid sequences include the production of RNA transcripts having more desirable properties, such as a greater half-life, than transcripts produced from the naturally occurring sequence.

The invention also encompasses production of DNA sequences, or fragments thereof, which encode LaeA and its derivatives, entirely by synthetic chemistry. After production, the synthetic sequence may be inserted into any of the many available expression vectors and cell systems using reagents that are well known in the art. Moreover, synthetic chemistry may be used to introduce mutations into a sequence encoding LaeA or any fragment thereof.

Also encompassed by the invention are nucleotide sequences that are capable of hybridizing to the claimed nucleic acids, and in particular, those that encode the amino acid sequence set forth in SEQ ID NO:3, under various conditions of stringency as taught in Wahl, G. M. and S. L. Berger (1987; Methods Enzymol. 152:399-407) and Kimmel, A. R. (1987; Methods Enzymol. 152:507-511), preferably highly stringent hybridization conditions, as defined herein.

Methods for DNA sequencing which are well known and generally available in the art and may be used to practice any of the embodiments of the invention. The methods may employ such enzymes as the Klenow fragment of DNA polymerase I, SEQUENASE.®. (US Biochemical Corp, Cleveland, Ohio), Taq polymerase (Perkin Elmer), thermostable T7 polymerase (Amersham, Chicago, Ill.), or combinations of polymerases and proofreading exonucleases such as those found in the ELONGASE Amplification System marketed by Gibco/BRL (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Me.) and the ABI Catalyst and 373 and 377 DNA Sequencers (Perkin Elmer).

The nucleic acid sequences encoding LaeA may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318-322). In particular, genomic DNA is first amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using commercially available software such as OLIGO 4.06 Primer Analysis software (National Biosciences Inc., Plymouth, Minn.), or another appropriate program, to be 22-30 nucleotides in length, to have a GC content of 50% or more, and to anneal to the target sequence at temperatures about 68.degree.-72.degree C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111-119). In this method, multiple restriction enzyme digestions and ligations may also be used to place an engineered double-stranded sequence into an unknown fragment of the DNA molecule before performing PCR. Another method which may be used to retrieve unknown sequences is that of Parker, J. D. et al. (1991; Nucleic Acids Res. 19:3055-3060). Additionally, one may use PCR, nested primers, and PROMOTER FINDER.™. libraries to walk genomic DNA (Clontech, Palo Alto, Calif.LIF.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled device camera. Output/light intensity may be converted to electrical signal using appropriate software (e.g. GENOTYPER.™. and SEQUENCE NAVIGATOR.™., Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, nucleotide sequences or fragments thereof which encode LaeA may be used in recombinant DNA molecules to direct expression of LaeA, fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express LaeA.

As will be understood by those of skill in the art, it may be advantageous to produce LaeA-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter LaeA-encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding LaeA may be ligated to a heterologous sequence to encode a fusion protein. For example, to screen peptide libraries for inhibitors of LaeA activity, it may be useful to encode a chimeric LaeA protein that can be recognized by a commercially available antibody. A fusion protein may also be engineered to contain a cleavage site located between the LaeA encoding sequence and the heterologous protein sequence, so that LaeA may be cleaved and purified away from the heterologous moiety.

In another embodiment, sequences encoding LaeA may be synthesized, in whole or in part, using chemical methods well known in the art (see Caruthers, M. H. et al. (1980) Nucl. Acids Res. Symp. Ser. 215-223, Horn, T. et al. (1980) Nucl. Acids Res. Symp. Ser. 225-232). Alternatively, the protein itself may be produced using chemical methods to synthesize the amino acid sequence of LaeA, or a fragment thereof. For example, peptide synthesis can be performed using various solid-phase techniques (Roberge, J. Y. et al. (1995) Science 269:202-204) and automated synthesis may be achieved, for example, using the ABI 431A Peptide Synthesizer (Perkin Elmer).

The newly synthesized peptide may be substantially purified by preparative high performance liquid chromatography (e.g., Creighton, T. (1983) Proteins, Structures and Molecular Principles, W H Freeman and Co., New York, N.Y.). The composition of the synthetic peptides may be confirmed by amino acid analysis or sequencing (e.g., the Edman degradation procedure; Creighton, supra). Additionally, the amino acid sequence of LaeA, or any part thereof, may be altered during direct synthesis and/or combined using chemical methods with sequences from other proteins, or any part thereof, to produce a variant polypeptide.

In order to express a biologically active LaeA, the nucleotide sequences encoding LaeA or functional equivalents, may be inserted into appropriate expression vector, i.e., a vector which contains the necessary elements for the transcription and translation of the inserted coding sequence. Methods which are well known to those skilled in the art may be used to construct expression vectors containing sequences encoding LaeA and appropriate transcriptional and translational control elements. These methods include in vitro recombinant DNA techniques, synthetic techniques, and in vivo genetic recombination. Such techniques are described in Sambrook, J. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York, N.Y.

A variety of expression vector/host systems may be utilized to contain and express sequences encoding LaeA. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems. The invention is not limited by the host cell employed.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, La Jolla, Calif.) or PSPORT1 plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding LaeA, vectors based on SV40 or EBV may be used with an appropriate selectable marker.

In bacterial systems, a number of expression vectors may be selected depending upon the use intended for LaeA. For example, when large quantities of LaeA are needed for the induction of antibodies, vectors which direct high level expression of fusion proteins that are readily purified may be used. Such vectors include, but are not limited to, the multifunctional E. coli cloning and expression vectors such as BLUESCRIPT.®. (Stratagene), in which the sequence encoding LaeA may be ligated into the vector in frame with sequences for the amino-terminal Met and the subsequent 7 residues of .beta.-galactosidase so that a hybrid protein is produced; pIN vectors (Van Heeke, G. and S. M. Schuster (1989) J. Biol. Chem. 264:5503-5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, Saccharomyces cerevisiae, a number of vectors containing constitutive or inducible promoters such as alpha factor, alcohol oxidase, and PGH may be used. For reviews, see Ausubel et al. (supra) and Grant et al. (1987) Methods Enzymol. 153:516-544.

In cases where plant expression vectors are used, the expression of sequences encoding LaeA may be driven by any of a number of promoters. For example, viral promoters such as the 35S and 19S promoters of CaMV may be used alone or in combination with the omega leader sequence from TMV (Takamatsu, N. (1987) EMBO J. 6:307-311). Alternatively, plant promoters such as the small subunit of RUBISCO or heat shock promoters may be used (Coruzzi, G. et al. (1984) EMBO J. 3:1671-1680; Broglie, R. et al. (1984) Science 224:838-843; and Winter, J. et al. (1991) Results Probl. Cell Differ. 17:85-105). These constructs can be introduced into plant cells by direct DNA transformation or pathogen-mediated transfection. Such techniques are described in a number of generally available reviews (see, for example, Hobbs, S. or Murry, L. E. in McGraw Hill Yearbook of Science and Technology (1992) McGraw Hill, New York, N.Y.; pp. 191-196).

An insect system may also be used to express LaeA. For example, in one such system, Autographa californica nuclear polyhedrosis virus (AcNPV) is used as a vector to express foreign genes in Spodoptera frugiperda cells or in Trichoplusia larvae. The sequences encoding LaeA may be cloned into a non-essential region of the virus, such as the polyhedrin gene, and placed under control of the polyhedrin promoter. Successful insertion of LaeA will render the polyhedrin gene inactive and produce recombinant virus lacking coat protein. The recombinant viruses may then be used to infect, for example, S. frugiperda cells or Trichoplusia larvae in which LaeA may be expressed (Engelhard, E. K. et al. (1994) Proc. Nat. Acad. Sci. 91:3224-3227).

In mammalian host cells, a number of viral-based expression systems may be utilized. In cases where an adenovirus is used as an expression vector, sequences encoding LaeA may be ligated into an adenovirus transcription/translation complex consisting of the late promoter and tripartite leader sequence. Insertion in a non-essential E1 or E3 region of the viral genome may be used to obtain a viable virus which is capable of expressing LaeA in infected host cells (Logan, J. and Shenk, T. (1984) Proc. Natl. Acad. Sci. 81:3655-3659). In addition, transcription enhancers, such as the Rous sarcoma virus (RSV) enhancer, may be used to increase expression in mammalian host cells.

Specific initiation signals may also be used to achieve more efficient translation of sequences encoding LaeA. Such signals include the ATG initiation codon and adjacent sequences. In cases where sequences encoding LaeA, its initiation codon, and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125-162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells which have specific cellular machinery and characteristic mechanisms for post-translational activities (e.g., CHO, HeLa, MDCK, HEK293, and W138), are available from the American Type Culture Collection (ATCC; Bethesda, Md.) and may be chosen to ensure the correct modification and processing of the foreign protein.

For long-term, high-yield production of recombinant proteins, stable expression is preferred. For example, cell lines which stably express LaeA may be transformed using expression vectors which may contain viral origins of replication and/or endogenous expression elements and a selectable marker gene on the same or on a separate vector. Following the introduction of the vector, cells may be allowed to grow in an enriched media before they are switched to selective media. The purpose of the selectable marker is to confer resistance to selection, and its presence allows growth and recovery of cells which successfully express the introduced sequences. Resistant clones of stably transformed cells may be proliferated using culture techniques appropriate to the cell type.

Any number of selection systems may be used to recover transformed cell lines. These include, but are not limited to, the herpes simplex virus thymidine kinase (Wigler, M. et al. (1977) Cell 11:223-32) and adenine phosphoribosyltransferase (Lowy, I. et al. (1980) Cell 22:817-23) genes which can be employed in tk.sup.- or aprt.sup.-cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567-70); npt, which confers resistance to the aminoglycosides neomycin and G-418 (Colbere-Garapin, F. et al (1981) J. Mol. Biol. 150:1-14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047-51). Recently, the use of visible markers has gained popularity with such markers as anthocyanins, .beta glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121-131).

Although the presence/absence of marker gene expression suggests that the gene of interest is also present, its presence and expression may need to be confirmed. For example, if the sequence encoding LaeA is inserted within a marker gene sequence, transformed cells containing sequences encoding LaeA can be identified by the absence of marker gene function. Alternatively, a marker gene can be placed in tandem with a sequence encoding LaeA under the control of a single promoter. Expression of the marker gene in response to induction or selection usually indicates expression of the tandem gene as well.

Alternatively, host cells which contain the nucleic acid sequence encoding LaeA and express LaeA may be identified by a variety of procedures known to those of skill in the art. These procedures include, but are not limited to DNA-DNA or DNA-RNA hybridizations and protein bioassay or immunoassay techniques which include membrane, solution, or chip based technologies for the detection and/or quantification of nucleic acid or protein.

The presence of polynucleotide sequences encoding LaeA can be detected by DNA-DNA or DNA-RNA hybridization or amplification using probes or fragments or fragments of polynucleotides encoding LaeA. Nucleic acid amplification based assays involve the use of oligonucleotides or oligomers based on the sequences encoding LaeA to detect transformants containing DNA or RNA encoding LaeA.

A variety of protocols for detecting and measuring the expression of LaeA, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on LaeA is preferred, but a competitive binding assay may be employed. These and other assays are described, among other places, in Hampton, R. et al. (1990; Serological Methods, a Laboratory Manual, APS Press, St Paul, Minn.) and Maddox, D. E. et al. (1983; J. Exp. Med. 158:1211-1216).

A wide variety of labels and conjugation techniques are known by those skilled in the art and may be used in various nucleic acid and amino acid assays. Means for producing labeled hybridization or PCR probes for detecting sequences related to polynucleotides encoding LaeA include oligolabeling, nick translation, end-labeling or PCR amplification using a labeled nucleotide. Alternatively, the sequences encoding LaeA, or any fragments thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn, (Kalamazoo, Mich.); Promega (Madison Wis.); and U.S. Biochemical Corp., (Cleveland, Ohio)). Suitable reporter molecules or labels, which may be used for ease of detection, include radionuclides, enzymes, fluorescent, chemiluminescent, or chromogenic agents as well as substrates, cofactors, inhibitors, magnetic particles, and the like Host cells transformed with nucleotide sequences encoding LaeA may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode LaeA may be designed to contain signal sequences which direct secretion of LaeA through a prokaryotic or eukaryotic cell membrane. Other constructions may be used to join sequences encoding LaeA to nucleotide sequence encoding a polypeptide domain which will facilitate purification of soluble proteins Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and LaeA may be used to facilitate purification. One such expression vector provides for expression of a fusion protein containing LaeA and a nucleic acid encoding 6 histidine residues preceding a thioredoxin or an enterokinase cleavage site. The histidine residues facilitate purification on IMAC (immobilized metal ion affinity Chromatography as described in Porath, J. et al. (1992, Prot. Exp. Purif. 3:263-281) while the enterokinase cleavage site provides a means for purifying LaeA from the fusion protein. A discussion of vectors which contain fusion proteins is provided in Kroll, D. J. et al. (1993; DNA Cell Biol. 12:441-453).

In addition to recombinant production, fragments of LaeA may be produced by direct peptide synthesis using solid-phase techniques (Merrifield J. (1963) J. Am. Chem. Soc. 85:2149-2154). Protein synthesis may be performed using manual techniques or by automation. Automated synthesis may be achieved, for example, using Applied Biosystems 431A Peptide Synthesizer (Perkin Elmer). Various fragments of LaeA may be chemically-synthesized separately and combined using chemical methods to produce the full length molecule.

In another embodiment, the present invention is a method of increasing the production of a secondary metabolite in a secondary metabolite-producing organism. Based upon the foregoing, one of skill in the art may transform a secondary metabolite-producing organism with a nucleic acid as described above as well as expression vectors comprising such nucleic acids. The nucleic acid is preferably over expressed following the transformation step resulting in an increase in secondary metabolite production in the transformed organism. The increase in secondary metabolite production is greater than 2 fold as compared to an untransformed control. The inventors have observed 400-900% increases in penicillin production in A. nidulans as well as 500-700% increases of lovastin in A. terreus. In certain embodiments, the secondary metabolite benefiting from increased production is lovastin, sterigmatocystin, penicillin, or gliotoxin. Preferred secondary metabolite-producing organisms include Aspergillus species, preferably A. nidulans or A. terreus or A. fumigatus. A detailed example of how such a method of increasing the production of a secondary metabolite may be carried out is described below in the EXAMPLES section.

In another embodiment directed to improving yields of secondary metabolites from host systems, the method according to the invention may utilize a non-secondary metabolite producing organism and include the additional step of transforming said organism with an entire biosynthetic gene cluster or at least biosynthetic genes sufficient for the production of a secondary metabolite or a secondary metabolite derivative or analog. The additional expression, preferably overexpression, of LaeA in the transformed organism may then enhance the production of a desired secondary metabolite.

In other embodiments, the secondary metabolite benefiting from increased production is a rare or minor secondary metabolite species that, without the amplification provided by the present invention, would not be present in amounts allowing identification and/or purification. Following amplification based on the present invention, dentification and purification of rare or minor species may, of course, be carried out by techniques known to the skilled artisan such as, for example, thin layer chromatography (TLC) followed by mass spectrometry (MS). Thus, it can be appreciated that the present invention provides a new and advantageous key to allow enhanced screening and identification of new and useful secondary metabolites.

In yet other embodiments of the invention, overexpression and/or deletion laeA strains may be utilized in novel screens for new and useful secondary metabolite biosynthesis gene clusters. For example, using standard microarray technology now commonly employed in the field, one of skill in the art may construct a microarray containing, for example, nucleic acids representative of the expressed genes of wild-type A. nidulans (see, for example, D. Bowtell and J. Sambrook, DNA Microarrays: A Molecular Cloning Manual (2000) Cold Spring Harbor Laboratory Press and P. Baldi and G. W. Hatfield, DNA Microarrays and Gene Expression: From Experiments to Data Analysis and Modeling (2002) Cambridge University Press describing standard microarray techniques data analyses applicable in the present invention). Construction of the specific nucleic acids affixed to the array substrate may be based on, for example, an expressed sequence tag database provided by the University of Oklahoma (see genome.ou.edu.fungal). Using the microarray and standard hybridization techniques known in the field, the expression levels of genes in wild-type A. nidulans versus an laeA deletion mutant may then be compared to identify genes whose expression is reduced or absent in the laeA deletion mutant compared to the wild-type line. The artisan may subsequently examine the genomic sequence available for A. nidulans in order to identify putative secondary metabolite biosynthesis cluster genes in the immediate vicinity of the relevant gene whose expression is initially identified as affected by the absence of laeA expression. As secondary metabolite biosynthesis genes are well known to occur in clustered fashion, as described in a plurality of references cited herein, new putative secondary metabolite gene clusters may be identified by this approach. Further, genes within a putative gene cluster may subsequently be disrupted and the mutant line's production of secondary metabolite products may then be compared with wild-type production in plus/minus fashion to identify the specific natural product produced by the newly-identified gene cluster. The natural product may then be isolated and characterized using standard techniques described and referenced herein.

It is envisioned the above-described screening strategies may be carried out not only between wild-type and laeA deletion mutants but also, and more preferably, between laeA overexpression mutants and laeA deletion mutants to obtain the greatest contrast in laeA-influenced secondary metabolite biosynthesis gene expression. As well, the screening methodology described herein is not limited to any one particular fungus but may be applied to any fungus having an laeA ortholog (e.g., Aspergillus other than A. nidulans). For example, the genome for Fusarium graminearum is now available and screens utilizing laeA overexpression or disruption strains to identify new F. graminearum secondary metabolite gene clusters may certainly be carried out based on the novel materials and teachings provided herein.

In order to demonstrate the utility of the above-described screening methodology, the inventors carried out differential gene expression analyses with a microarray using unique sequences available from an A. nidulans expressed sequence tag database (through the University of Oklahoma website genome.ou.edu.fungal). In addition, approximately 145 gene sequences from GenBank that are not represented in the EST database were included, as well as the sequence for laeA (provided herein). The resulting array represented 6,529 unique gene sequences; this is a substantial portion of the approximately 10,000 expressed genes of the A. nidulans genome. Probe sequences of 24 base pairs were created and estimated to provide approximately 14 sequences per gene. These sequences were synthesized on chips by Nimblegen, Inc. (Madison, Wis.), using proprietary maskless technology. Total RNA was prepared from FGSC 26 (biA1; veA1) and RJW40.7 (biA1; ΔlaeA::metG;veA1) using TRIzol® reagent (Invitrogen, Carlsbad, Calif.) followed by RNeasy clean up (Qiagen Inc., Valencia, Calif.). The fungal strains used for this procedure are further detailed in Table 1 below. Total RNA was spiked with control RNA transcripts, converted to biotinylated cRNA and fragmented following the Affymetrix Expression Analysis Technical Manual (rev 1). Hybridization mixtures were prepared according to the array manufacturer's standard protocol using 10 mg biotinylated cRNA. Samples were incubated with the arrays overnight at 42° C. Chips were washed, stained with streptavadin-linked Cy3 dye, and dried according to the manufacturer's protocol. Chips were scanned using a GenePix scanner (Axon Instruments, Union City, Calif.). The data were converted to a Microsoft Access database and normalized by the RNA spike control signals. Genes dependent on LaeA for expression were determined by expression ratios (wild type to mutant deleted laeA strain). Among the lowests ratios were genes known to be involved in penicillin and sterigmatocystin biosynthesis, consistent with other experimental data. Two additional LaeA-dependent genes were found to be adjacent to each other in the *A. nidulans* genome sequence (now annotated as AN8439.1 and AN8440.1). These genes are within 10 kb of genes encoding a non-ribosomal peptide synthase (AN8433.1), a tyrosinase (AN8435.1), and a P450 monooxygenase (AN8437.1), enzymes that are hallmarks of secondary metabolic pathways. Thus, the method according to the present invention was useful in the initial step of identifying a putative secondary metabolite biosynthesis gene cluster. This putative cluster is now available to be further characterized and defined using standard methodologies.

The present invention is also a method of inhibiting or reducing production of a secondary metabolite by replacement of the naturally-occurring laeA or a laeA homologue with a polynucleotide encoding a variant of the polypeptide as set forth in SEQ ID NO: 3 wherein the variant is altered by mutagenesis or equivalent technique to be non-functional in terms of increasing or regulating secondary metabolite production. Such a gene replacement exercise could be carried out by one of skill in the art using techniques presently known in the field. Such a method would be useful in reducing or eliminating production of toxic secondary metabolites in certain organisms. For example, a non-functional variant of laeA would be useful in reducing or eliminating aflatoxin production in an *A. parasiticus* or *A. flavus* strain transformed thereby (e.g., the ΔlaeA strains described in the following section are illustrative of this method). In addition, LaeA may be targeted by a therapeutic such that LaeA's ability to regulate secondary metabolite gene cluster activity is inhibited. This approach would provide a therapeutic able to reduce the virulence of cells or organisms thereby providing a treatment for medical maladies involving fungal infections. Methods of identifying inhibitors of target molecules are well known in the art.

In another embodiment, the present invention includes the transformed organisms described above. These organisms include secondary metabolite-producing organisms, preferably yeast and fungi, that have been engineered to display at least a 2 fold increase in secondary metabolite production, preferably where the secondary metabolites are lovastatin or pencillin. These organisms also include non-secondary metabolite-producing organisms, preferably yeast or fungi, that have been engineered to produce secondary metabolites. Transformed organisms may comprise a nucleic acid described above as well as expression vectors including such a nucleic acid.

The following examples are offered for illustrative purposes only, and are not intended to limit the scope of the present invention in any way. Indeed, various modifications of the invention in addition to those shown and described herein will become apparent to those skilled in the art from the foregoing description and fall within the scope of the appended claims.

IV. EXAMPLES

A. Materials and Methods

Fungal Strains and Growth Conditions

Table 1 lists all fungal strains used herein. Some strains are not discussed in the text but were used for sexual crosses to obtain the strains of interest. Sexual crosses of *A. nidulans* strains were conducted according to Pontecorvo et al.[26] All strains were maintained as glycerol stocks and were grown at 37° C. for *A. nidulans* and *A. fumigatus* or 32° C. for *A. terreus* on glucose minimal medium (GMM)[46], threonine minimal medium (TMM)[16] or lactose minimal medium (LMM)[9] amended with 30 mM cyclopentanone. Threonine and cyclopentanone both induce alcA(p) which was used to promote laeA expression. All media contained appropriate supplements to maintain auxotrophs[27].

TABLE 1

Fungal strains.

| Fungal Strains | Genotype | Source |
|---|---|---|
| Wild type and controls | | |
| *Aspergillus nidulans* strains | | |
| FGSC 26 | biA1; veA1' | FGSC[a] |
| RDIT 2.1 | methG1 | D. Tsitsigiannis |
| RAMB38 | biA1; methG1; ΔaflR::argB, trpC801, veA1 | A. M. Bergh |
| RDIT 2.3 | veA1 | D. Tsitsigiannis |
| RDIT 7.24 | methG1; veA1 | D. Tsitsigiannis |
| RDIT 30.34 | methG1; trpC801; pyrG89; veA1 | D. Tsitsigiannis |
| RJH26 | biA1; wA3; argB2; ΔstcE::argB, veA1, trpC801 | this study |
| RJW3 | pyrG89; wA3; argB2; pyroA4; ΔstcE::argB, veA1, trpC801 | this study |
| RJW51 | alcA(p)::lovB::pyr4; hygromycinB::lov gene cluster | this study |
| RKIS 1 | pabaA1, yA2; veA1 | 39 |
| RMFV2 | pabaA1, yA2; veA1, argB2; ΔaflR::argB | 40 |
| TJH3.40 | biA1; wA3; argB2; methG1; ΔstcE::argB2, veA1 | 41 |
| TJH34.10 | pabaA1, yA2; veA1, alcA(p)::aflR::trpC | 42 |
| TPK1.1 | biA1; methG1; veA1 | N. Keller |
| WMH1739 | pabaA1, yA2, alcA(p)::lovB::pyr4; hygromycinB::lov gene cluster | 43 |
| *A. fumigatus* strains | | |
| AF293 | | G. May |
| AF293.1 | pyrG⁻ | G. May |
| TJW55.2 | pyrG⁻, *A. parasiticus* pyrG | this study |
| *A. terreus* strains | | |
| ATCC 20542 | | ATCC[b] |
| TJW58.9 | hygB | this study |
| laeA mutants | | |
| *Aspergillus nidulans* strains | | |
| MRB300 | biA1; wA3; methG1; ΔstcE::argB2; veA1; laeA1 | 41 |
| RJW32 | biA1; wA3; argB2; methG1; ΔstcE::argB, veA1, trpC801 ΔlaeA::methG | this study |
| RJW33.2 | wA3; argB2; methG1; pyroA4; ΔstcE::argB, veA1, trpC801; ΔlaeA::methG | this study |
| RJW 40.4 | biA1; methG1; veA1; ΔlaeA::methG | this study |
| RJW 40.7 | biA1; ΔlaeA::methG; veA1 | this study |
| RJW 44.2 | biA1; methG1; alcA(p)::laeA::trpC, veA1; ΔlaeA::methG | this study |
| RJW 46.4 | methG1; veA1; ΔlaeA::methG | this study |
| RJW 54.8 | methG1; aflR::trpC, veA1; ΔlaeA::methG | this study |
| RJW 55.8 | methG1; aflR::trpC, ΔaflR::argB, veA1; ΔlaeA::methG | this study |
| RYJ 8 | biA1; wA3; ΔstcE::argB, veA1, trpC801; laeA1 | this study |
| RJW52 | alcA(p)::laeA::trpC; alcA(p)::lovB::pyr4; hygromycinB::lov gene cluster | this study |
| RJW53 | ΔlaeA::methG; alcA(p)::lovB::pyr4; hygromycinB::lov gene cluster | this study |

TABLE 1-continued

Fungal strains.

| Fungal Strains | Genotype | Source |
|---|---|---|
| TJW46.16 | biA1; wA3; argB2; methG1; ΔstcE::argB, veA1; alcA(p)::gfp::laeA::trpC; ΔlaeA::methG | this study |
| TJW57.9 | wA3; argB2; methG1; pyroA4; ΔstcE::argB, veA1, aflR::trpC; ΔlaeA::methG | this study |
| *A. fumigatus* strain | | |
| TJW54.2 | ΔlaeA::*A. parasiticus* pyrG; pyrG⁻ | this study |
| *A. terreus* strains | | |
| TJW58.2 | hygB; alcA(p)::laeA | this study |
| TJW58.4 | hygB; alcA(p)::laeA | this study |
| TJW58.7 | hygB; alcA(p)::laeA | this study |
| TJW58.8 | hygB; alcA(p)::laeA | this study |
| TJW58.14 | hygB; alcA(p)::laeA | this study |
| Signal transduction mutants | | |
| H1FAD4 | biA1; veA1; fadA^{G42R} | 44 |
| RKIS 11.1 | pabaA1, yA2; veA1, argB2; ΔfadA::argB | 45 |
| RKIS 28.5 | pabaA1, yA2; veA1, alcA(p)::ras^{A17V}::argB | 45 |
| TBN39.5 | biA1; methG1; argB2; ΔflbA::argB; veA1 | 46 |
| TJH34.10 | pabaA1, yA2; trpC801, trpC::alcA::aflR, veA1 | J. Hicks |
| TKIS 18.11 | pabaA1, yA2; ΔargB::trpC; trpC801, veA1; ΔpkaA::argB | 45 |
| TKIS20.1 | pabaA1, yA2; veA1, alc(p)::pkaA::trpC | 45 |
| TSRB1.38 | biA1; methG1; argB2; ΔsfaD::argB; veA1 | 407 |

[a]FGSC = Fungal Genetics Stock Center,
[b]ATCC = American type culture collection Cloning and Sequence of the *A. nidulans* and *A. fumigatus* laeA Genes The *A. nidulans* aflR expression mutant, RYJ8 (derived from MRB300, see Supplementary Information), was transformed with an *A. nidulans* genomic cosmid library. Norsolorinic acid (NOR) producing transformants were purified and a cosmid, pCOSJW3, that complemented the mutation was rescued from one transformant. NOR is a visible precursor in the ST biosynthetic pathway and commonly used as an indicator of ST production[5] pJW15, a 4.5 kb KpnI-EcoRI subclone of pCOSJW3 also complemented the mutation and was sequenced using synthetic primers and ABI PRISM DNA sequencing kit (PerkinElmer Life Science). The mutant allele, laeA1, was sequenced after subcloning a 3 kb PCR fragment from RYJ8 genomic DNA amplified with primers LAE1 and LAE2 (see Supplementary Information) into Zero Blunt TOPO vector (Invitrogen Co.) to produce pJW31. RACE technology using Gene Racer Kit (Invitrogen Co.) was employed to clone laeA cDNA according to manufacturer's instruction. The cloned cDNA was then sequenced. The Institute for Genomic Research (TIGR) contains partial *A. fumigatus* genome sequence (/tigr.org/tdb/e2k1/afu1/). A putative *A. fumigatus* laeA homolog was obtained by blasting the *A. fumigatus* data with the *A. nidulans* laeA sequence.

Nucleic Acid Analysis

Extraction of DNA from fungi and bacteria, restriction enzyme digestion, gel electrophoresis, blotting, hybridization and probe preparation were performed by standard methods[16, 28]. Total RNA was extracted from *Aspergillus* strains using Trizol reagent (Invitrogen Co.) according to the manufacturer's instructions. RNA blots were hybridized with a 0.7 kb SacII-KpnI fragment from pRB7 containing the stcU coding region[18], a 1.3 kb EcoRV-XhoI fragment from pJW19 containing the aflR coding region, a 3 kb HindIII fragment from pJW45.4 containing the laeA coding region, a 1.1 kb EcoRI-HindIII fragment from pUCHH(458) containing the ipnA coding region[29], a 5 kb BamHI fragment from pWHM1401 containing the lovE coding region[9], and a 1.3 kb PCR product from pWHM1263 containing the lovC coding region[9]. Also *A. nidulans* cosmids pWO7H03, pL11C09 and pL24B03 were used as probes. pL11C09 contains most of the ST gene cluster, whereas pW07H03 and pL24B03 primarily contain genes located upstream and downstream of the ST gene cluster, respectively[8].

Fungal Transformation Procedures

Fungal transformation essentially followed that of Miller et al.[30] with the modification of embedding the protoplasts in top agar (0.75%) rather than spreading them by a glass rod on solid media.

Methyltransferase Bioassay

Nuclei of wild type and ΔlaeA strains were extracted from cultures grown in GMM liquid media at 37° C., 300 rpm for 36 h. The mycelia were pulverized in liquid nitrogen with a buffer (1.0M sorbitol, 10 mM Tris.HCl, pH7.5) and then subjected to centrifugation (Sorvall GSA rotor, 2500 rpm for 10 min). Supernatants were transferred to new tubes and centrifuged at 10,000 rpm for 15 min to isolate nuclei. The isolated nuclei were collected in 1.5 ml centrifuge tubes and 200 µl adenosyl-L-(methyl-³H) methionine [Amersham Pharmacia Biotech., 76.0 Ci/mmol, 1 mCi/ml in dilute HCl (pH2.0):ethanol 9:1, v/v)] was added to 1 ml. The reaction mixture was incubated 3 h at 30° C. and then nuclear protein was extracted using Trizol reagent (Invitrogen Co.) according to the manufacturer's instructions. Protein extracts (160 µg) were separated on a 10% SDS PAGE gel and the dried gel was exposed on X-ray film for one month.

Construction of Transformation Vectors and Strains

Plasmids were generated using standard techniques. Primers are listed in Table 2. pfu Turbo (Stratagene Co.) was used for PCR reactions. The *A. nidulans* disruption plasmid pJW34 was constructed by ligating a 1.2 kb DNA fragment upstream of the laeA start codon (primers Lae1 and LA2) and a 1.2 kb DNA fragment downstream of the laeA stop codon (primers LA3 and Lae2) to either side of the methG gene in the pUGI1-41 vector[31]. The 5' end PCR product and 3' end PCR product were inserted into the SacI site and HindIII site of pUG11-41 by blunt end ligation, respectively. pJW34 was used to disrupt the laeA gene (ΔlaeA) in TJH3.40 to create TJW35.5. TJW35.5 was subsequently sexually crossed to RDIT2.1 to create RJW46.4. Plasmid pJW47.4 was constructed to over express laeA from the alca promoter[32]. The 2.5 kb coding sequence of laeA was amplified with primers OEF and OER and ligated into the HindIII site of pCN2 which contains the 5' half of the trpC gene and the alca promoter[2]. This resulted in an alcA(p)::laeA fusion referred to as OE::laeA in text. pJW47.4 was used to transform RJW32 to tryptophan auxotrophy to yield the strain TJW44.39. TJW44.39 was subsequently sexually crossed to RDIT2.1 to create RJW47.3. pJW47.4 and a hygromycynB (hygB) resistance gene containing plasmid pUCH2-8[33] were used for cotransformation to introduce the over expression laeA construct into *A. terreus* ATCC20542. Transformants were selected in hygromycin B (500 µg/ml) containing medium and confirmed by PCR and Southern hybridization. Five transformants, TJW58.2, TJW58.4, TJW58.7, TJW58.8 and TJW58.14 containing hygB and OE::laeA, were examined for LOV production and TJW58.9 containing hygB alone was used as a control (Table 1). pJW45.4, containing a wild type copy of the laeA gene, was used to complement the ΔlaeA FUM1 and FUM2), and a 1.0 kb DNA fragment downstream of the laeA stop cordon (primers FUM3 and FUM4) on either side of the *A. parasiticus* pyrG marker gene obtained from pBZ5[37]. pJW58 was used to disrupt the *A. fumigatus* laeA gene in strain AF293.1 to create TJW54.2.

TABLE 2

Primers

| Primer | Sequence[a] | Restriction sites | SEQ ID NO: |
|---|---|---|---|
| LAE1 | ATCTACCTTTCTGGGCTCCTGG | | 4 |
| LAE2 | CGTGAAGAACTTGGCGTTGTAG | | 5 |
| LA2 | GACGAGCTCGTGGAACAGTGGAAGGAAC | SacI | 6 |
| LA3 | GCGAAGCTTATGAACCGCATCAACCGA | HindIII | 7 |
| OEF | GCTGTGAAGCTTTGTACCCTGTTTCGCC | HindIII | 8 |
| OER | GATTTGAAGCTTTGCTGGCATGGAACGG | HindIII | 9 |
| MT1 | ATGCTGAAGCTTGGAAACTGGGAAAGGGTC | HindIII | 10 |
| GFP2 | TGACGAATTCTCTTAATGGTTTCCTAGCCTG | EcoRI | 11 |
| GFP31 | TGCGGAATTCATGAGCAAGGGCGAGGAA | EcoRI | 12 |
| GFP4 | GGATGCCTCGAGTTTGTACAGCTCGTCCATGC | XhoI | 13 |
| GFP5 | AAGCAGCTCGAGTAAGAGCAAAAGGCGACCAC | XhoI | 14 |
| GF1 | CTAGCGAAGCTTGCCACCATGAGCAAGGGCG | HindIII | 15 |
| GF2 | CGGCGAATTCCTTGTACAGCTCGTCCATGC | EcoRI | 16 |
| GF3 | TTTGGAATTCGTTTCGCCGCTGATGTTTGAG | EcoRI | 17 |
| FUM1 | GCGCACTTCTTTGTTTTCCCCT | | 18 |
| FUM2 | CATCGGAATTCTTTCTTGAGCGGCC | EcoRI | 19 |
| FUM3 | TACCAGGATCCAAAACCTCTCGCCA | BamHI | 20 |
| FUM4 | CATGACGGTAACTAAGGATTTGG | | 21 |

[a]underlined sequences show placement of restriction sites shown on the right.

strain RJW33.2. pJW45.4 was created by ligating the 3 kb laeA gene (primers MT1 and OER) into the Hin III site of pSH96. pSH96 contains the 5′ half of the trpC gene[34]. RJW33.2 is a sexual progeny of a cross between TJW35.5 and RJW3. pJW45.4 was used to transform RJW33.2 to produce TJW42.7. TJW42.7 was crossed with RDIT7.24 sexually to create RJW49.1. Plasmids pJW48 and pJW49 were created to visualize LaeA by fusing the green fluorescent protein (sGFP) gene[35,36] to the N-terminal and C-terminal of LaeA, respectively. pJW48 was made by ligating the 0.7 kb gfp gene (primers GF1 and GF2) to 5′ end of the 2.5 kb encoding region of laeA gene (primers GF3 and OER) and then the ligated fragment was inserted into the pCN2 HinIII site to yield the alcA(p)::gfp::laeA chimera. pJW49 was constructed by consecutively ligating a 2 kb laeA coding region (primers OEF and GFP2), a 0.7 kb gfp gene (primers GFP31 and GFP4), and a 0.5 kb laeA termination cassette (primers GFP5 and OER) into the Hin III site in pCN2 to yield an alcA(p)::laeA::gfp::laeAterm chimera. pJW48 and pJW49 were used to transform RJW32 to yield transformants TJW46.16 (5′ GFP) and TJW47.9 (3′ GFP) respectively. The *A. fumigatus* laeA gene disruption vector, pJW58, was constructed by inserting a 0.9 kb DNA fragment upstream of the laeA start cordon (primers Secondary Metabolite Analysis.

Published procedures were used to extract and analyze ST[6], gliotoxin[1], lovastatin[9] and monocolin J[9]. Further details are available in references cited herein. ST was extracted from either GMM 50 ml shake cultures inoculated with $10^7$ spores/ml grown for 60 hours or solid media cultures spread with $10^6$ spores/plate grown for 5 days. Dried ST extracts were resuspended in 100 μl chloroform and 10 μl was separated in chloroform:acetone (8:2) on TLC plates. ST (Sigma Chem Co) was spotted as a standard. MONJ was extracted from 50 ml GMM shake cultures inoculated with 107 spores/ml grown for 72 hours. MONJ from WT:lov+ and OE::laeA; lov+ strains was extracted from cultures grown in 50 ml liquid shaking GMM for 14 h at 37° C. and then transferred to liquid shaking threonine minimal media (TMM) for 24 h. Dried MONJ extracts were resuspended in 100 μl methanol and 10 μl was separated in methanol:0.1% phoshoric acid (9:1) on C-18 reversed phase TLC plates. MONJ standard was extracted from *A. nidulans* strain WMH1739 (Table 1). All experiments were triplicated. Gliotoxin production in *A. fumigatus* was analyzed by modification of the TLC method of Belkacemi et al.[38]. Gliotoxin was extracted from 50 ml GMM shake cultures inoculated with $10^7$ spores/ml grown for 3 days. Dried chloroform extracts were resuspended in 100 μl methanol and 10 μl was separated in chloroform: methanol (9:1). Gliotoxin (Sigma Chem Co.) was spotted as a standard. All experiments were triplicated. To assess PN production, *Micrococcus luteus* ATCC 9341 was grown on TBS (Bacto Trypton 17 g, Bacto Soyton 3 g, NaCl 5 g, $K_2HPO_4$ 2.5 g and glucose 2.5 g in 1 liter) at 37° C. 180 rpm until O.D.=1.3.3 ml of *M. luteus* culture was mixed with 40 ml TSA (Bacto Trypton 15 g, Bacto Soyton 5 g, NaCl 5 g, and agar 10 g in 1 liter) and poured in 150 cm diameter plates to solidify. Fifty ml cultures of WT, ΔlaeA and OE::laeA strains ($10^7$ spores/ml) were grown in liquid shaking GMM for 14 h at 37° C. and then transferred to liquid shaking LMM amended with 30 mM cyclopentanone for 24 h. For each strain, six ml were removed, lyophilized and resuspended in 1 ml distilled water. One hundred μl samples, with or without 6 units β-lactamase, were placed in 10 cm wells of the *M. luteus* plates. Plates were placed for 2 h at 4° C. and then incubated overnight at 37° C. to evaluate PN inhibition zones. All experiments were duplicated. Lovastatin was extracted from *A. terreus* cultures grown in 50 ml liquid shaking GMM for 18 h at 32° C. and then transferred to liquid shaking LMM with 30 mM cyclopentanone for 36 h at 32° C. Extraction and identification on TLC were followed by the previously described method in MONJ examination. Lovastatin (Merk. Co.) was spotted as a control. All experiments were duplicated.

B. Cloning of the laeA Gene and Characterization of the Encoded Polypeptide.

The greatest number of known fungal secondary metabolites has been ascribed to the *Ascomycete* genus *Aspergillus*. Studies of *Aspergillus nidulans* have demonstrated the power of using a model system to elucidate the molecular genetics of fungal secondary metabolism, principally penicillin (PN, an antibiotic) and sterigmatocystin (ST, a carcinogen biochemically related to the agricultural contaminant aflatoxin) biosynthesis (reviewed in Brakhage[2] and Hicks et al.[3] respectively). These studies have established several characteristics of fungal secondary metabolism including clustering of biosynthetic and regulatory genes as well as a genetic connection linking secondary metabolite biosynthesis with sporulation through a shared signal transduction pathway[1]. The inventors were interested in identifying global regulators of secondary metabolism in fungi that can uncouple the sporulation process from secondary metabolite production. Such regulatory elements are extremely desirable because they would possess broad specificity for the activation and/or repression of secondary metabolite genes while providing strains capable of otherwise normal or near-normal development and growth.

Figure 5:
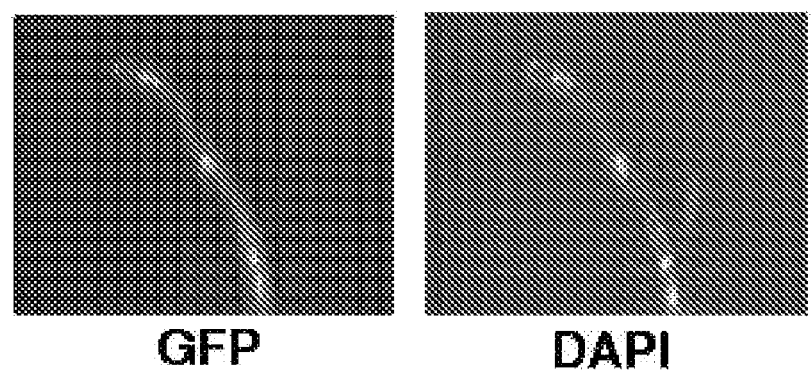
FIG. 5. *Aspergillus nidulans* LaeA protein localizes to the nucleus. The green fluorescent protein (GFP) was fused to LaeA and as described herein. Nuclei were stained with the DNA-specific dye 4,6-diamindino-2-phenylindole (DAPI).
Figure 6:
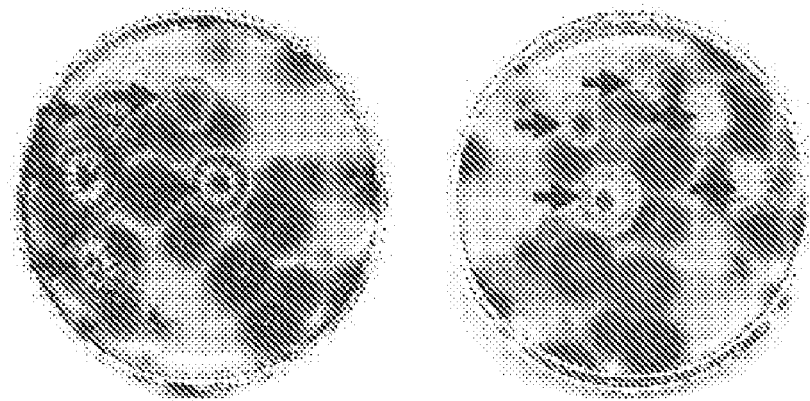
FIG. 6. *Aspergillus fumigatus* transformants. Left is the top view of the petri dish and right the bottom view. Arrows indicate strains with a disrupted laeA gene.

Previously a mutagenesis screen led to isolation of 23 mutants displaying loss of ST production but normal sporulation in *A. nidulans*[5]. Three of the mutants were unable to express aflR that encodes a ST cluster $Zn_2Cys_6$ transcription factor regulating ST biosynthetic gene expression[6]. The inventors were able to complement one of these three mutants, RYJ8, with an *A. nidulans* trpC genomic cosmid library. Sequencing of a 4.5 kb subclone (pJW15) of the complementing cosmid pCOSJW3 revealed a 3 kb ORF designated as laeA (for loss of aflR expression). Sequencing of the mutant allele, laeA1, from RYJ8 showed it has a base pair transversion (1455; C->G) and a one base pair deletion (1453 bp) of the gene. The deletion resulted in a premature stop codon. Examination of genomic and cDNA sequence revealed that laeA has one intron and three putative AflR binding sites[6], one in the promoter (–607) and two in the encoding region (607 and 1487, FIG. 1a). cDNA analysis showed laeA possesses a 5' untranslated region (642 bp) (FIG. 1a). Analysis of available genomic databases indicated only filamentous fungi have obvious LaeA homologs including *A. fumigatus* (human pathogen, aspergillosis TIGR (tigr.org/tdb/e2k1/afu1/), *Neurospora crassa* (model fungus, GenBank™), *Magnaporthe grisea* (plant pathogen, rice blast fungus), *Coccidioides immitis* (human pathogen, coccidioidomycosis, GenBank) and *Fusarium sporotrichioides* (plant pathogen, trichothecene mycotoxin producer (genome.o-u.edu/fsporo) (FIG. 1b). Examination of the LaeA amino acid sequence (375 amino acids) revealed a conserved s-adenosylmethionine (SAM) binding site found exclusively in nuclear protein methyltransferases (FIG. 1b)[7]. Although the amino acid sequence of LaeA did not show the presence of a nuclear localization motif, green fluorescent protein (sGFP) tagging to either the 5' or the 3' end of *A. nidulans* laeA showed LaeA to be localized in the nucleus (FIG. 5). Biochemical analysis showed that LaeA methylated a ca. 30 kDa nuclear protein (FIG. 1c).

laeA null mutants (ΔlaeA) were created by replacing laeA with methG and pyrG in *A. nidulans* TJH3.40 (a methG1 auxotroph) and *A. fumigatus* AF293.1 (a pyrG auxotroph), respectively. Southern and PCR analyses were carried out to confirm single gene replacement events in several transformants including *A. nidulans* TJW35.5 and *A. fumigatus* TJW54.2. Prototroph RJW46.4 was obtained from TJW35.5 by a sexual cross as described in the materials and methods section. RJW46.4 and TJW54.2 were used for this study. In both spp., ΔlaeA strains were visually detectable due to loss of mycelial pigment in the backside of colonies (FIG. 2a and FIG. 6). An examination of organic extracts of *A. nidulans* and *A. fumigatus* ΔlaeA strains showed that production of several metabolites were reduced, including ST in *A. nidulans* (FIG. 2b) and the immunotoxin gliotoxin in *A. fumigatus* (FIG. 2c). A verification that these defects were caused by loss of laeA was obtained by transforming *A. nidulans* ΔlaeA with wild type laeA and observing remediation of metabolite production.

Figure 7:
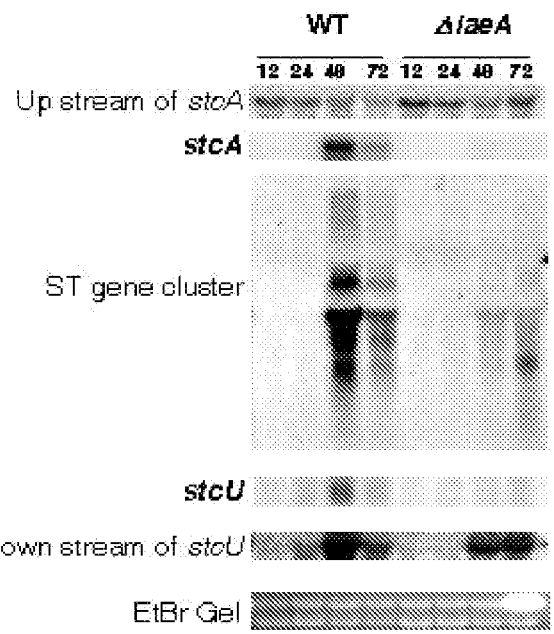
FIG. 7. Transcript analysis of the ST gene cluster and genes immediately upstream and downstream of the gene cluster. *A. nidulans* WT (RDIT2.3) and ΔlaeA (RJW46.4) strains were grown in liquid shaking GMM for 12 h, 24 h, 48 h and 72 h at 37° C. stcA and stcU are two characterized ST biosynthetic genes at either end of the ST gene cluster[48]. Ethidium bromide stained rRNA is indicated for loading.

To confirm the initial observation that laeA is required for ST gene regulation, the inventors assessed aflR and stcU (a gene encoding a biosynthetic enzyme required for ST production)[3] expression in the ΔlaeA background. Neither gene was expressed (FIG. 3a). A transcriptional profile of the entire ST gene cluster, which covers ca. 60 kb and contains ca. 26 genes[8], suggests LaeA transcriptional control is ST cluster specific as transcription of upstream and downstream genes of the ST cluster are unaffected (FIG. 7). Because many uncharacterized metabolites were reduced in the ΔlaeA strains (FIG. 2b), the inventors believed it possible that LaeA could be a global regulator for secondary metabolite gene expression. To address this hypothesis, the inventors examined PN gene expression in the ΔlaeA strain. FIG. 3a shows that ipnA (a gene encoding isopenicillin N synthetase, a biosynthetic enzyme required for PN biosynthesis)[2] expression was greatly reduced in the ΔlaeA strain. The inventors' results of ST and PN gene expression suggested a role for LaeA in secondary metabolite gene cluster regulation. To further address this potential role, the inventors examined the expression of the heterologous LOV gene cluster in the *A. nidulans* ΔlaeA background. The partial LOV cluster, derived from *A. terreus*, was originally transformed into *A. nidulans* to study aspects of lovastatin biosynthesis[9]. This strain was used to cross the LOV cluster (LOV+) into appropriate laeA mutant backgrounds. FIG. 3b shows the ΔlaeA; LOV+strain displayed greatly diminished levels of both lovE (a LOV specific $Zn_2Cys_6$ transcription factor) and lovC (a LOV biosynthetic gene) transcripts. Organic extracts of this strain also showed diminished production of monocolin J, MONJ (FIG. 3b), the LOV intermediate produced by the partial LOV cluster[9].

The inventors next constructed laeA over expression strains (OE::IaeA) in both *A. nidulans* and *A. terreus* to examine secondary metabolite gene expression and product formation. As shown in FIG. 3c, ipnA, lovE, lovC but not stcU expression were remarkably elevated in the *A. nidulans* OE::laeA background. Secondary metabolite production was correlated with transcript levels. MONJ production was increased 400% and high levels of PN where produced during times when wild type showed no PN activity (FIG. 3d). ST levels remained the same as wild type in the OE::laeA background (FIG. 3c). Over expression of the *A. nidulans* laeA gene in the lovastatin producing fungus, *A. terreus*, led to 400-700% increases in LOV (FIG. 3e).

Figure 8:
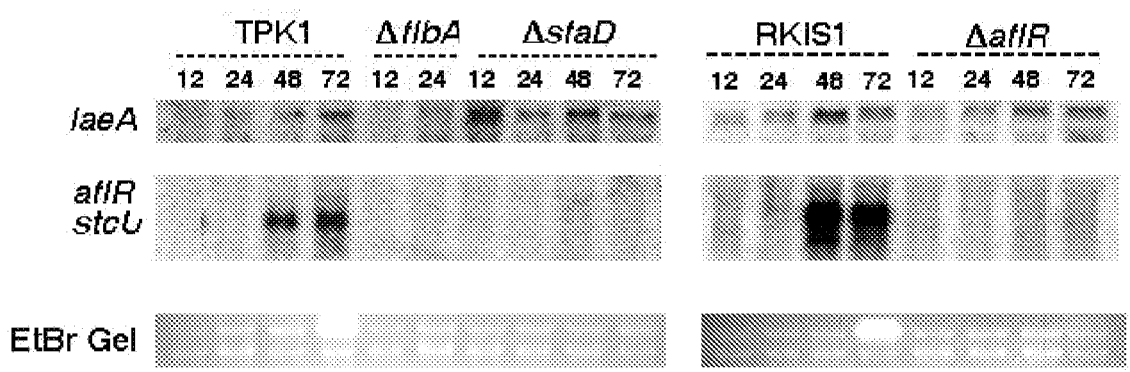
FIG. 8. laeA expression is not affected in ΔflbA, ΔsfaD and ΔaflR strains. laeA, aflR and stcU gene expression in *A. nidulans* WT (TPK1.1, RKIS1), ΔflbA (TBN39.5), ΔsfaD (TSRB1.38), and ΔaflR (RMFV2) strains grown in liquid shaking GMM for 12 h, 24 h, 48 h and 72 h at 37° C. Ethidium bromide stained rRNA is indicated for loading.

The steady state levels of ST transcripts and product formation in the OE::laeA background in contrast to increased PN and LOV transcripts and product formation suggested a unique interaction between laeA and ST gene regulation. Due to the presence of three AflR binding sites in the *A. nidulans* gene (FIG. 1a), the inventors thought it possible that AflR might regulate laeA expression. As shown in FIG. 3f, over expression of aflR (OE::aflR) down regulates laeA expression although elimination of aflR (ΔaflR) does not affect laeA transcript (FIG. 8). This indicates both negative (laeA) and positive (stc genes)[6] regulatory effects of AflR on gene transcription. To the inventors' knowledge, this is the first description of a putative secondary metabolite feedback mechanism. As overproduction of ST negatively affects fungal growth the inventors speculate this feedback loop may have evolved as a fitness trait. In contrast, neither the promoter or encoding region of *A. fumigatus* laeA contained AflR binding sites nor was an aflR ortholog found in the genome. Initial examinations of the *Aspergillus* ΔlaeA strains showed them to be more susceptible to neutrophil kill than wild type. Presumably this is due to loss of toxin secondary metabolites or melanins, known virulence factors in several fungal systems[11,12].

Figure 4:
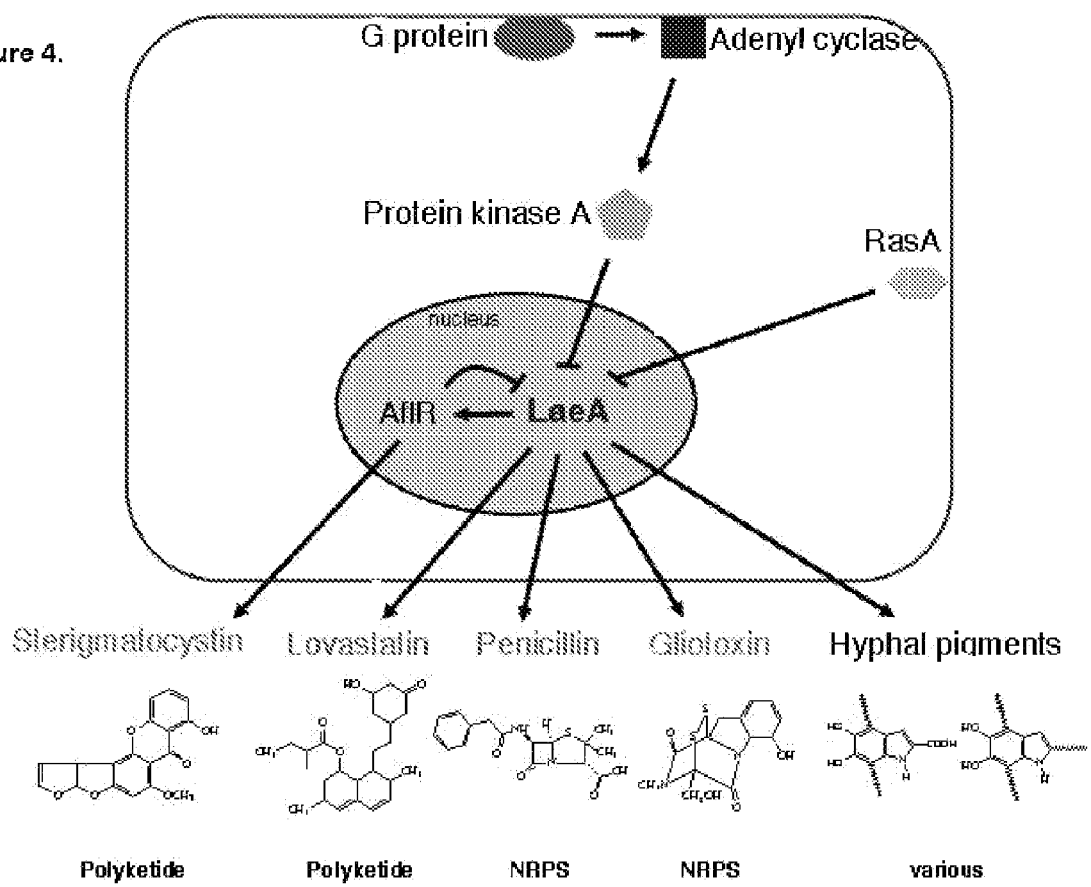
FIG. 4. Schematic of LaeA's putative role as a global regulator of secondary metabolisms.
Figure 9:
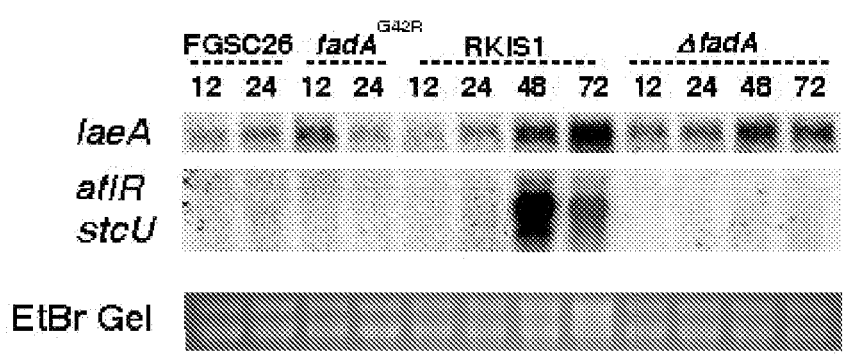
FIG. 9. laeA expression is not affected in fadA mutants. laeA, aflR and stcU gene expression in *A. nidulans* WT(FGSC26), ΔfadAG42R(H1FAD4) and WT(RKIS1), ΔfadA (RKIS11.1) strains grown in liquid shaking GMM for 12 h, 24 h, 48 h and 72 h at 37° C. Ethidium bromide stained rRNA is indicated for loading.

ST biosynthesis is regulated in *A. nidulans* via a signal transduction pathway and many of the genes involved in this signaling pathway are known[1]. Therefore, the inventors looked at the possible interactions with laeA of five signaling genes encoding two members of a heterotrimeric G protein (fadA and sfaD)[13,14], a regulator of G-protein signaling protein regulating FadA activity (flbA)[15], a cAMP dependent kinase (pkaA)[16] and a Ras protein (rasA)[17]. laeA expression was examined in wild type and strains carrying the following alleles: ΔflbA, fadA$^{G42R}$, ΔfadA, ΔsfaD, ΔpkaA, OE:pkaA, and OE::rasA$^{G17A}$ (see Table 1). mRNA analysis of these mutants showed that OE::pkaA and OE::rasA$^{G17A}$ completely inhibited laeA expression (FIG. 3f) whereas laeA transcription was not affected in any of the other strains (FIG. 8). Presence of laeA transcript in the ΔflbA and fadA$^{G42R}$ mutants (FIG. 8 and FIG. 9) shows that laeA is not sufficient for aflR expression as aflR is not expressed in these strains[18]. FIG. 4 thusly depicts the inventors' current understanding of LaeA involvement in secondary metabolite regulation.

The requirement of a kinase for laeA function is reminiscent—to a degree—of a *Streptomyces* global regulatory system involving the protein AfsR. AfsR is a transcription factor regulating secondary metabolism in *S. coelicolor* but morphogenesis in *S. griseus* (contrast to the similar role LaeA has in the three *Aspergillus* spp. examined here). Phosphorylation of AfsR enhances its activity[19]. Like AfsR, LaeA regulation is at the transcriptional level but functionally, LaeA appears most similar to histone (HMTase) or arginine methyltransferases that play important roles in regulating gene expression in eukaryotes[7,20,21]. An interesting aspect of HMTase regulation has been the recent discovery that histone methylation plays a role in defining boundaries of euchromatic and heterochromatic chromosomal domains such as in the mating locus of yeast and the beta-globin locus in mice[22,23]. These findings suggest that histone methylation may be important in the regulation of gene cluster boundaries and may support a relationship with LaeA and histones in the regulation of secondary metabolite gene clusters. Also, studies of gene regulation in the *A. nidulans* PN gene cluster and the *A. nidulans* nitrate utilization gene cluster have shown that chromatin remodeling and/or DNA conformational changes are required for expression of genes in these clusters[24,25]. It is possible that ΔlaeA strain may be impaired in a type of cluster regulation that could be revealed through biochemical tests addressing DNA conformational changes. Regardless of mechanism, and none is expressly adopted herein, the identification of LaeA presents a significant advance in understanding the complex regulation of secondary metabolite production and provides a platform for biotechnological manipulations of their production. Manipulation of LaeA in filamentous fungi enables the increased production of pharmaceuticals and the elimination of fungal toxins by providing improved strains of engineered organisms and also contributes to the broader understanding of molecular mechanisms by which secondary metabolites are produced.

Those skilled in the art will recognize, or be able to ascertain using no more then routine experimentation, numerous equivalents to the specific polypeptides, nucleic acids, methods, assays and reagents described herein. Such equivalents are considered to be within the scope of this invention and covered by the following claims. All publications, patents, and patent applications cited herein are hereby incorporated by reference in their entirety for all purposes.

V. REFERENCES

1. Calvo, A. M., Wilson, R. A., Bok, J. W. & Keller, N. P. Relationship between secondary metabolism and fungal development. *Microbiol. Mol. Biol. Rev.* 66, 447-459 (2002).
2. Brakhage, A. A. Molecular regulation of beta-lactam biosynthesis in filamentous fungi. *Microbiol. Mol. Biol. Rev.* 62, 547-585 (1998).
3. Hicks, J. K., Shimizu, K. & Keller N. P., in The Mycota, Kempken, F. & Bennett, Eds. (Spring-Verlag, 2002), Vol. XI, chap 4.
4. Hawksworth, D. L. The magnitude of fungal diversity: the 1.5 million species estimate revisited. *Mycol. Res.* 105, 1422-1432 (2001).
5. Butchko, R. A., Adams, T. H. & Keller, N. P. *Aspergillus nidulans* mutants defective in stc gene cluster regulation. *Genetics* 153, 715-720 (1999).
6. Fernandes, M., Keller, N. P. & Adams, T. H. Sequence-specific binding by *Aspergillus nidulans* AflR, a C6 zinc cluster protein regulating mycotoxin biosynthesis. *Mol. Microbiol.* 28, 1355-1365 (1998).
7. Hamahata, A., Takata, Y., Gomi, T. & Fujioka, M. Probing the S-adenosylmethionine-binding site of rat guanidinoacetate methyltransferase. Effect of site-directed mutagenesis of residues that are conserved across mammalian non-nucleic acid methyltransferases. *Biochem. J.* 317, 141-145 (1996).
8. Brown D. W. et al Twenty-five coregulated transcripts define a sterigmatocystin gene cluster in *Aspergillus nidulans*. *Proc. Natl. Acad. Sci. USA* 93, 1418-1422 (1996).

9. Kennedy, J. et al. Modulation of polyketide synthase activity by accessory proteins during lovastatin biosynthesis. *Science* 284, 1368-1372 (1999).
10. Hah, H. Differential action of cercoran and topsin-M on sensitive and tolerant strains of toxic fungi. *Cryptogamie Mycologie* 14, 61-68 (1993).
11. Belkacemi, L., Barton, R. C., Hopwood, V. & Evans, E. G. V. Determination of optimum growth conditions for gliotoxin production by *Aspergillus fumigatus* and development of a novel method for gliotoxin detection. *Medical Mycology* 37, 227-233 (1999).
12. Langfelder, K., Streibel, M., Jahn, B., Haase, G. & Brakhage, A. A. Biosynthesis of fungal melanins and their importance for human pathogenic fungi. *Fungal Genet. Biol.* 38, 143-158 (2003).
13. Yu, J.-H., Wieser, J. & Adams, T. H. The *Aspergillus* FlbA RGS domain protein antagonizes G protein signaling to block proliferation and allow development. *EMBO J.* 15, 5184-5190 (1996).
14. Rosén, S., Yu, J.-H. & Adams, T. H. The *Aspergillus nidulans* sfaD gene encodes a G protein beta subunit that is required for normal growth and repression of sporulation. *EMBO J.* 18, 5592-5600 (1999).
15. Lee, B. N. & Adams, T. H. Overexpression of flbA, an early regulator of *Aspergillus* asexual sporulation, leads to activation of brlA and premature initiation of development. *Mol. Microbiol.* 14, 323-334 (1994).
16. Shimizu, K. & Keller, N. P. Genetic involvement of a cAMP-dependent protein kinase in a G protein signaling pathway regulating morphological and chemical transitions in *Aspergillus nidulans*. *Genetics* 157, 591-600 (2001).
17. Som, T & Kolaparthi, V. S. Developmental decisions in *Aspergillus nidulans* are modulated by Ras activity. *Mol. Cell Biol.* 14, 5333-5348 (1994).
18. Hicks, J. K., Yu, J.- H., Keller, N. P. & Adams, T. H. *Aspergillus* sporulation and mycotoxin production both require inactivation of the FadA G alpha protein-dependent signaling pathway. *EMBO J.* 16, 4916-4923 (1997).
19. Umeyama, T., Lee, P. C. & Horinouchi, S. Protein serine/threonine kinases in signal transduction for secondary metabolism and morphogenesis in *Streptomyces*. *Appl. Microbiol. Biotechnol.* 59, 419-425 (2002).
20. Tamaru, H. & Selker, E. U. A histone H3 methyltransferase controls DNA methylation in *Neurospora crassa*. *Nature*, 414, 277-283 (2001).
21. Mowen, K. A. et al Arginine methylation of STAT1 modulates IFN alpha/beta-induced transcription. *Cell*, 104, 731-741 (2001).
22. Litt, M. D., Simpson, M., Gaszner, M., Allis, C. D. & Felsenfeld, G. Correlation between histone lysine methylation and developmental changes at the chicken beta-globin locus. *Science* 293, 2453-2455 (2001).
23. Noma, K., Allis, C. D. & Grewal, S. I. Transitions in distinct histone H3 methylation patterns at the heterochromatin domain boundaries. *Science* 293, 1150-1155 (2001).
24. Litzka, O., Papagiannopolus, P., Davis, M. A., Hynes, M. J. & Brakhage, A. A. The penicillin regulator PENR1 of *Aspergillus nidulans* is a HAP-like transcriptional complex. *Eur. J. Biochem.* 251, 758-767 (1998).
25. Muro-Pastor, M. I., Gonzalez, R., Strauss, J., Narendja, F. M. & Scazzocchio, C. The GATA factor AreA is essential for chromatin remodelling in a eukaryotic bidirectional promoter. *EMBO J.* 18, 1584-1597 (1999).
26. Pontecorvo, G., Roper, J. A., Hemmons, L. M., Macdonald, K. P. & Bufton, A. W. J. The genetics of *Aspergillus nidulans*. *Adv. Gen.* 5, 141-238 (1953).
27. Adams, T. H. & Timberlake, W. E. Developmental repression of growth and gene expression in *Aspergillus*. *Proc. Natl. Acad. Sci. USA* 87, 5405-5409 (1990).
28. J. Sambrook, E. F. Fritsch, T. Maniatis, *Molecular Cloning: A Laboratory Manual* (Cold Spring Harbor Lab. Press, Plainview, N.Y.) (1989).
29. Tilbum, J. et al. The *Aspergillus* PacC zinc finger transcription factor mediates regulation of both acid- and alkaline-expressed genes by ambient pH. *EMBO J.* 14, 779-790 (1995).
30. Miller, B. L., Miller, K. Y. & Timberlake, W. E. Direct and indirect gene replacements in *Aspergillus nidulans*. *Mol. Cell Biol.* 5, 1714-1721 (1985).
31. Sienko M. & Paszewski, A. The mehtG gene of *Aspergillus nidulans* encoding cystathionine beta-lyase: cloning and analysis. *Curr. Genet.* 35, 638-646 (1999).
32. Hicks, J. K. et al. RcoA has pleiotropic effects on *Aspergillus nidulans* cellular development *Mol. Microbiol.* 39, 1482-1493 (2001).
33. Alexander, N.J., Hohn, T. H. & McCormick, S. P. The TRI11 gene of *Fusarium sporotrichioides* encodes a cytochrome P-450 monooxygenase required for C-15 hydroxylation in trichothecene biosynthesis. *Appl. Environ. Microbiol.* 64, 221-225 (1998).
34. Wieser, J. & Adams, T. H. flbD encodes a Myb-like DNA-binding protein that coordinates initiation of *Aspergillus nidulans* conidiophore development. *Genes Dev.* 9, 491-502 (1995).
35. Chalfie, M., Tu, Y., Euskirchen, G., Ward, W. W. & Prasher, D. C. Green fluorescent protein as a marker for gene expression. *Science* 263, 802805 (1994).
36. Fernandez-Abalos, J. M., Fox, H., Pitt, C., Wells, B. & Doonan, J. H. Plant-adapted green fluorescent protein is a versatile vital reporter for gene expression, protein localization and mitosis in the filamentous fungus, *Aspergillus nidulans*. *Mol. Microbiol.* 27, 121-130 (1998).
37. Skory, C. D., Chang, P. K., Cary, J. & Linz, J. E. Isolation and characterization of a gene from *Aspergillus parasiticus* associated with the conversion of versicolorin A to sterigmatocystin in aflatoxin biosynthesis. *Appl. Environ. Microbiol.* 58, 3527-3537 (1992).
38. Belkacemi, L., Barton, R. C., Hopwood, V. & Evans, E. G. V. Determination of optimum growth conditions for gliotoxin production by *Aspergillus fumigatus* and development of a novel method for gliotoxin detection. *Medical Mycology* 37, 227-233 (1999).
39. Adams, T. H. & Timberlake, W. E. Developmental repression of growth and gene expression in *Aspergillus*. *Proc. Natl. Acad. Sci. USA* 87, 5405-5409 (1990).
40. Fernandes, M., Keller, N. P. & Adams, T. H. Sequence-specific binding by *Aspergillus nidulans* AflR, a C6 zinc cluster protein regulating mycotoxin biosynthesis. *Mol. Microbiol.* 28, 1355-1365 (1998).
41. Kennedy, J. et al. Modulation of polyketide synthase activity by accessory proteins during lovastatin biosynthesis. *Science* 284, 1368-1372 (1999).
42. J. Sambrook, E. F. Fritsch, T. Maniatis, *Molecular Cloning: A Laboratory Manual* (Cold Spring Harbor Lab. Press, Plainview, N.Y.) (1989).
43. Tilbum, J. et al. The *Aspergillus* PacC zinc finger transcription factor mediates regulation of both acid- and alkaline-expressed genes by ambient pH. *EMBO J.* 14, 779-790 (1995).
44. Yu, J.-H., Wieser, J. & Adams, T. H. The *Aspergillus* FlbA RGS domain protein antagonizes G protein signaling to block proliferation and allow development. *EMBO J.* 15, 5184-5190 (1996).

45. Shimizu, K. & Keller, N. P. Genetic involvement of a cAMP-dependent protein kinase in a G protein signaling pathway regulating morphological and chemical transitions in *Aspergillus nidulans*. *Genetics* 157, 591-600 (2001).
46. Lee, B. N. & Adams, T. H. Overexpression of flbA, an early regulator of *Aspergillus* asexual sporulation, leads to activation of brlA and premature initiation of development. *Mol. Microbiol.* 14, 323-334 (1994).
47. Rosén, S., Yu, J.-H. & Adams, T. H. The *Aspergillus nidulans* sfaD gene encodes a G protein beta subunit that is required for normal growth and repression of sporulation. *EMBO J.* 18, 5592-5600 (1999).
48. Brown D. W. et al Twenty-five coregulated transcripts define a sterigmatocystin gene cluster in *Aspergillus nidulans*. *Proc. Natl. Acad. Sci. USA* 93, 1418-1422 (1996).

What is claimed is:

1. A method for identifying a novel secondary metabolite biosynthesis gene cluster in a fungus, said method comprising steps of:
   a) obtaining a transformed fungus having a disrupted laeA gene wherein said laeA gene before disruption comprises a nucleotide sequence that encodes a nuclear protein methyltransferase and that hybridizes under stringent conditions, comprising overnight hybridization at 42° C. in 50% formamide with 1 mg heparin followed by a 15 minute wash at 65° C. in 0.2x SSC, to either strand of a denatured double-stranded nucleic acid having the nucleotide sequence set forth in SEQ ID NO:2; and wherein expression of the non-disrupted laeA gene in a fungal host cell results in the increased production of a polypeptide capable of regulating a gene cluster specifying the production of at least one secondary metabolite selected from a polyketide, a non-ribosomal peptide and a hyphal pigment and expression of a disrupted laeA gene results in the production of an inactive laeA polypeptide or its absence;
   (b) isolating a sample of nucleic acids from the transformed fungus of step (a), said sample of nucleic acids representative of the expressed genes of the transformed fungus;
   (c) hybridizing the sample of nucleic acids isolated in step (b) with an array comprising a plurality of nucleic acids representative of the expressed genes of a non-transformed fungus under conditions to form one or more hybridization complexes;
   (d) detecting said hybridization complexes;
   (e) comparing the levels of the hybridization complexes detected in step (c) with the level of hybridization complexes detected in a sample of nucleic acids isolated from an laeA-expressing fungus and representative of the expressed genes of the laeA-expressing fungus, wherein an altered level of hybridization complexes detected in step (c) compared with a level of hybridization complexes of the sample of the nucleic acids from the laeA-expressing fungus correlates with an identifies at least one gene under regulatory control of the laeA gene product; and
   (f) examining genomic nucleotide sequence surrounding said gene identified in step (e) to determine if said gene is clustered with secondary metabolite biosynthesis genes thereby identifying a novel secondary metabolite biosynthesis gene cluster.

2. A method according to claim 1, wherein said nucleic acids representative of the expressed genes of the non-transformed fungus in step (c) are immobilized on a substrate.

3. A method according to claim 1, wherein said nucleic acids representative of the expressed genes of the non-transformed fungus in step (c) are hybridizable elements in a microarray.

4. A method according to claim 1, wherein the sample of nucleic acids isolated from the laeA-expressing fungus and representative of the expressed genes of the laeA-expressing fungus in step (e) are isolated from a transformed fungus overexpressing laeA gene product as compared to the non-transformed fungus.

5. A method according to claim 1 wherein the fungus is an *Aspergillus* or *Fusarium* species.

* * * * *